United States Patent
Stoddard et al.

(10) Patent No.: US 10,837,024 B2
(45) Date of Patent: Nov. 17, 2020

(54) MODIFYING MESSENGER RNA STABILITY IN PLANT TRANSFORMATIONS

(71) Applicant: CELLECTIS, Paris (FR)

(72) Inventors: Thomas Stoddard, St. Louis Park, MN (US); Song Luo, Chicago, IL (US)

(73) Assignee: CELLECTIS, Paris (FR)

( * ) Notice: Subject to any disclaimer, the term of this patent is extended or adjusted under 35 U.S.C. 154(b) by 94 days.

(21) Appl. No.: 15/056,544

(22) Filed: Feb. 29, 2016

(65) Prior Publication Data

US 2017/0081672 A1   Mar. 23, 2017

Related U.S. Application Data

(60) Provisional application No. 62/219,842, filed on Sep. 17, 2015.

(51) Int. Cl.
| | |
|---|---|
| *C12N 15/82* | (2006.01) |
| *A01H 4/00* | (2006.01) |
| *C12N 9/22* | (2006.01) |
| *C12N 15/52* | (2006.01) |

(52) U.S. Cl.
CPC ......... *C12N 15/8213* (2013.01); *A01H 4/008* (2013.01); *C12N 9/22* (2013.01); *C12N 15/52* (2013.01); *C12N 15/8241* (2013.01); *C12Y 301/00* (2013.01); *C12N 2840/10* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,683,195 A | 7/1987 | Mullis et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,959,317 A | 9/1990 | Sauer |
| 4,975,374 A | 12/1990 | Goodman et al. |
| 5,006,333 A | 4/1991 | Saifer et al. |
| 5,013,659 A | 5/1991 | Bedbrook et al. |
| 5,162,602 A | 11/1992 | Somers et al. |
| 5,204,253 A | 4/1993 | Sanford et al. |
| 5,276,268 A | 1/1994 | Strauch et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,501,967 A | 3/1996 | Offringa et al. |
| 5,538,880 A | 7/1996 | Lundquist et al. |
| 5,554,798 A | 9/1996 | Lundquist et al. |
| 5,561,236 A | 10/1996 | Leemans et al. |
| 5,591,616 A | 1/1997 | Hiei et al. |
| 5,767,366 A | 6/1998 | Sathasivan et al. |
| 5,792,640 A | 8/1998 | Chandrasegaran |
| 5,879,903 A | 3/1999 | Strauch et al. |
| 5,928,937 A | 7/1999 | Kakefuda et al. |
| 6,084,155 A | 7/2000 | Volrath et al. |
| 6,326,166 B1 | 12/2001 | Pomerantz et al. |
| 6,329,571 B1 | 12/2001 | Hiei |
| 6,368,227 B1 | 4/2002 | Olson |
| 6,410,329 B1 * | 6/2002 | Hansen ............... C12N 15/8201 435/468 |
| 6,451,732 B1 | 9/2002 | Beckett et al. |
| 6,451,735 B1 | 9/2002 | Ottaway et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,001,768 B2 | 2/2006 | Wolffe |
| 7,013,219 B2 | 3/2006 | Case et al. |
| 7,067,722 B2 | 6/2006 | Fillatti |
| 7,070,934 B2 | 7/2006 | Cox, III et al. |
| 7,163,824 B2 | 1/2007 | Cox, III et al. |
| 7,189,691 B2 | 3/2007 | Hemenway |
| 7,220,719 B2 | 5/2007 | Case et al. |
| 7,262,054 B2 | 8/2007 | Jamieson et al. |
| 7,273,923 B2 | 9/2007 | Jamieson et al. |
| 7,285,416 B2 | 10/2007 | Choo et al. |
| 7,361,635 B2 | 4/2008 | Miller et al. |
| 7,521,241 B2 | 4/2009 | Choo et al. |
| 7,842,489 B2 | 11/2010 | Arnould et al. |
| 8,420,782 B2 | 4/2013 | Bonas et al. |
| 8,440,431 B2 | 5/2013 | Voytas et al. |

(Continued)

FOREIGN PATENT DOCUMENTS

| | | |
|---|---|---|
| EP | 0 242 246 | 10/1987 |
| EP | 2 206 723 | 7/2010 |

(Continued)

OTHER PUBLICATIONS

Wilkie G.S. et al. Regulation of mRNA translation by 5'- and 3'-UTR-binding factors. Trends Biochem Sci. Apr. 2003;28(4):182-8. Review. (Year: 2003).*

McCammon et al. Using zinc finger nucleases for efficient and heritable gene disruption in zebrafish. Methods Mol Biol. 2010;649: 281-98 (Year: 2010).*

"*Arabidopsis thaliana* polynucleotide SEQ ID No. 75774," Retrieved from EBI Accession No. GSM:A0E62298, Database Accession No. A0E62298 sequence, Feb. 3, 2011, 1 page.

"*Arabidopsis thaliana* mRNA for putative ER6 protein, complete cds, clone: RAFL14-67-K13," Retrieved from EBI Accession No. EM_STD:AK228228 Database Accession No. AK228228 sequence, Jul. 27, 2006, 1 page.

Egelkrout et al., "Overproduction of recombinant proteins in plants," Plant Science, 184: 83-101, Dec. 9, 2011.

(Continued)

*Primary Examiner* — Cynthia E Collins
(74) *Attorney, Agent, or Firm* — Fish & Richardson P.C.

(57) ABSTRACT

Materials and methods for genome engineering through transient expression of a targeted nuclease are described herein. For example, the methods described herein can include introducing into a cell a messenger RNA (mRNA) that encodes a nuclease targeted to a selected sequence within the cell, where the stability of the mRNA is modified by the addition of untranslated regions (UTRs).

9 Claims, 8 Drawing Sheets

Specification includes a Sequence Listing.

(56) References Cited

U.S. PATENT DOCUMENTS

| | | | |
|---|---|---|---|
| 8,440,432 | B2 | 5/2013 | Voytas et al. |
| 8,450,471 | B2 | 5/2013 | Voytas et al. |
| 8,586,363 | B2 | 11/2013 | Voytas et al. |
| 8,697,853 | B2 | 4/2014 | Voytas et al. |
| 9,035,129 | B2 | 5/2015 | Bilyeu et al. |
| 9,198,365 | B2 | 12/2015 | Bilyeu et al. |
| 9,914,930 | B2 * | 3/2018 | Cogan .................... C12N 15/79 |
| 2001/0016956 | A1 | 8/2001 | Ward et al. |
| 2005/0064474 | A1 | 3/2005 | Umov et al. |
| 2007/0141038 | A1 | 6/2007 | Choulika et al. |
| 2009/0060921 | A1 | 3/2009 | Dickey et al. |
| 2009/0133158 | A1 | 5/2009 | Lahaye et al. |
| 2009/0271881 | A1 | 10/2009 | Arnould et al. |
| 2009/0305402 | A1 | 12/2009 | Liljedahl et al. |
| 2010/0132069 | A1 | 5/2010 | Lahaye et al. |
| 2010/0154081 | A1 | 6/2010 | Weterings et al. |
| 2011/0041195 | A1 | 2/2011 | Doyon |
| 2011/0129898 | A1 | 6/2011 | Doyon et al. |
| 2011/0136895 | A1 | 6/2011 | Gregory et al. |
| 2011/0145940 | A1 | 6/2011 | Voytas et al. |
| 2011/0158957 | A1 | 6/2011 | Bonini et al. |
| 2011/0167521 | A1 | 7/2011 | DeKelver et al. |
| 2011/0201055 | A1 | 8/2011 | Doyon et al. |
| 2011/0201118 | A1 | 8/2011 | Yang et al. |
| 2011/0203012 | A1 | 8/2011 | Dotson et al. |
| 2011/0207221 | A1 | 8/2011 | Cost et al. |
| 2011/0239315 | A1 | 9/2011 | Bonas et al. |
| 2011/0247089 | A1 | 10/2011 | Doyon |
| 2011/0265198 | A1 | 10/2011 | Gregory et al. |
| 2011/0269234 | A1 | 11/2011 | Doyon et al. |
| 2011/0287545 | A1 | 11/2011 | Cost et al. |
| 2011/0301073 | A1 | 12/2011 | Gregory et al. |
| 2012/0110685 | A1 | 5/2012 | Bonas et al. |
| 2012/0122205 | A1 | 5/2012 | Bonas et al. |
| 2012/0178131 | A1 | 7/2012 | Voytas et al. |
| 2012/0178169 | A1 | 7/2012 | Voytas et al. |
| 2012/0214228 | A1 | 8/2012 | Voytas et al. |
| 2012/0246764 | A1 | 9/2012 | Hlubek et al. |
| 2012/0284877 | A1 | 11/2012 | Hlubek et al. |
| 2012/0324603 | A1 | 12/2012 | Hlubek et al. |
| 2013/0122581 | A1 | 5/2013 | Voytas et al. |
| 2014/0090116 | A1 | 3/2014 | Ainley et al. |

FOREIGN PATENT DOCUMENTS

| | | |
|---|---|---|
| EP | 2 392 208 | 12/2011 |
| EP | 2 562 260 | 2/2013 |
| WO | WO 1994/18313 | 8/1994 |
| WO | WO 1995/09233 | 4/1995 |
| WO | WO 2004/067736 | 8/2004 |
| WO | WO 2007/060495 | 5/2007 |
| WO | WO 2008/141806 | 11/2008 |
| WO | WO 2009/095793 | 8/2009 |
| WO | WO 2010/079430 | 7/2010 |
| WO | WO 2010/091018 | 8/2010 |
| WO | WO 2010/145846 | 12/2010 |
| WO | WO 2011/005998 | 1/2011 |
| WO | WO 2011/017293 | 2/2011 |
| WO | WO 2011/019385 | 2/2011 |
| WO | WO 2011/072246 | 6/2011 |
| WO | WO 2011/100058 | 8/2011 |
| WO | WO 2011/117249 | 9/2011 |
| WO | WO 2011/146121 | 11/2011 |
| WO | WO 2011/154393 | 12/2011 |
| WO | WO 2012/106105 | 8/2012 |
| WO | WO 2013/050155 | 4/2013 |
| WO | WO 2014/039692 | 3/2014 |
| WO | WO 2014/039702 | 3/2014 |
| WO | WO 2014/199358 | 12/2014 |

OTHER PUBLICATIONS

Eibl et al., "In vivo analysis of plastid psbA, rbcL and rpl32 UTR elements by chloroplast transformation: Tobacco plastid gene expression is controlled by modulation- of transcript levels and translation efficiency," The Plant J., 19(3):333-345, Aug. 1, 1999.

Ferizi et al., "Stability analysis of chemically modified mRNA using micropattern-based single-cell arrays," Lab on a chip: Miniaturisation for Chemistry, Physics, Biology, Materials Science and Bioengineering, 15(17):3561-3571, Jul. 16, 2015.

Gallie et al., "Introduction of MRNA to Plant Protoplast Using Polyethylene Glycol," Plant Cell Reports, 13:119-122, Jan. 1, 1993.

Huang et al., "Effect of the untranslated region and signal peptide sequence of the insecticidal gene from pseudomonas pseudoalcaligenes on the activity of its expression products in tobacco," World J Microbiology Biotechnology, 25(4):619-625, Dec. 14, 2008.

International Search Report and Written Opinion of International Application No. PCT/IB2016/055554, dated Dec. 5, 2016, 14 pages.

U.S. Appl. No. 61/225,043, filed Jul. 13, 2009, Bonas et al.

"TAL effector nucleases," Nature Reprint Collection [online]. Oct. 2011, [retrieved on Mar. 14, 2012]. Retrieved from the Internet: URL <http://www.nature.com/nbt/collections/talen/index.html>, 32 pages, Marshall (ed.).

Alam and Sittman, "Characterization of the cytotoxic effect of a chimeric restriction enzyme, H1°-FokI," Gene Ther Mol Biol, 10:147-160, 2006.

Alam, "Characterization of the cytotoxic effect of a novel chimeric restriction nuclease, H1°-FokI, in mouse fibroblast cells: Implications for chromatin mapping and gene therapy studies," Ph.D. Thesis, The University of Mississippi Medical Center, 223 pages, 2006.

Al-Saadi et al., "All five host-range variants of Xanthomonas citri carry one pthA homolog with 17.5 repeats that determines pathogenicity on citrus, but none determine host-range variation," Mol Plant Microbe Interact, 20(8): 934-943, 2007.

Antony et al., "Rice xa13 recessive resistance to bacterial blight is defeated by induction of the disease susceptibility gene Os-11N3," Plant Cell, 22(11):3864-3876, 2010.

Antony, "Molecular basis of avrXa7 mediated virulence in bacterial blight of rice," [abstract of dissertation] Kansas State University, 99 pages, 2010.

Aoyama and Chua, "A glucocorticoid-mediated transcriptional induction system in transgenic plants," The Plant Journal, 11:605-612, 1997.

Arimondo et al., "Exploring the cellular activity of camptothecintriple-helix-forming oligonucleotide conjugates," Mol Cell Biol, 26:324-333, 2006.

Athinuwat et al., "*Xanthomonas axonopodis* pv. glycines soybean cultivar virulence specificity is determined by avrBs3 homolog avrXgl," Phytopathology, 99(8):996-1004, 2009.

Bai et al., "*Xanthomonas oryzae* pv. oryzae avirulence genes contribute differently and specifically to pathogen aggressiveness," Mol Plant Microbe Interact, 13(12):1322-1329, 2000.

Baker, "Gene-editing nucleases," Nature Methods, 2012, 9:23-26.

Ballvora et al., "Genetic mapping and functional analysis of the tomato Bs4 locus governing recognition of the Xanthomonas campestris pv. vesicatoria AvrBs4 protein," Mol Plant Microbe Interact, 14(5):629-638, 2001.

Barry et al., "Differential expression of the 1-aminocyclopropane-1-carboxylate oxidase gene family of tomato," Plant J., 9:525-535, 1996.

Bashirullah et al., "Spatial and temporal control of RNA stability," Proc. Natl. Acad. Sci. USA, 98(13):7025-7028, 2001.

Belahj et al., "Plant genome editing made easy: targeted mutagenesis in model and crop plants using the CRISPR/Cas system," Plant Methods, 9:39 (2013).

Beretta et al., "Tethering a type IB topoisomerase to a DNA site by enzyme fusion to a heterologous site-selective DNA-binding protein domain," Cancer Res, 59:3689-3697, 1999.

Bethke and Busse, "Validation of a simple, colorimetric, microplate assay using amplex red for the determination of glucose and sucrose in potato tubers and other vegetables," Am. J. Pot Res.,.85:414-421 (2008).

Beuselinck et al., "An Assessment of Phenotype Selection for Linolenic Acid Using Genetic Markers," Crop Sci, 47:747-750 (2006).

(56) References Cited

OTHER PUBLICATIONS

Bhaskar et al., "Suppression of the vacuolar invertase gene prevents cold-induced sweetening in potato," Plant Physiol., 154(2):939-948 (Oct. 2010).
Bibikova et al., "Enhancing gene targeting with designed zinc finger nucleases," Science, 300(5620):764, 2003.
Bibikova et al., "Stimulation of homologous recombination through targeted cleavage by chimeric nucleases," Mol Cell Biol, 21(1): 289-297, 2001.
Bitinaite et al., "FokI dimerization is required for DNA cleavage," Proc Natl Acad Sci USA, 95:10570-10575, 1998.
Boch and Bonas. "Xanthomonas AvrBs3 family-type III effectors: discovery and function." Annu Rev Phytopathol, 48, 419-436, 2010.
Boch et al., "Breaking the code of DNA binding specificity of TAL-type III effectors," Science, 326:1509-1512, 2009.
Boch et al., "Molecular characterization of three AvrBs3-like effectors from the *Arabidopsis* pathogen *Xanthomonas campestris* pv. armoraciae," (abstract), XIV International Congress on Molecular Plant-Microbe Interactions, Quebec City, Canada, Jul. 19-23, 2009, 2 pages.
Bogdanove et al., "TAL effectors: Customizable Proteins for DNA Targeting," Science, 333:1843-1846, 2011.
Bogdanove et al., "TAL effectors: finding plant genes for disease and defense," Curr Opin Plant Biol, 13:394-401, 2010.
Bogue et al., "Developmentally regulated expression of a sunflower 11S seed protein gene in transgenic tobacco," Mol. Gen. Genet., 222:49-57, 1990.
Boller and He, "Innate immunity in plants: an arms race between pattern recognition receptors in plants and effectors in microbial pathogens," Science, 324:742-744, 2009.
Bonas et al., "Resistance in tomato to Xanthomonas campestris pv vesicatoria is determined by alleles of the pepper-specific avirulence gene avrBs3," Mol Gen Genet, 328: 261-269, 1993.
Bonas et al., "Genetic and structural characterization of the avirulence gene avrBs3 from Xanthomonas campestris pv. Vesicatoria," Mol Gen Genet, 218:127-136, 1989.
Bonas et al., "How the bacterial plant pathogen Xanthomonas campestris pv. vesicatoria conquers the host," Mol Plant Pathol, 1(1):73-76, 2000.
Bonas, "How Xanthomonas manipulates the plant cell," (abstract), XIV International Congress on Molecular Plant-Microbe Interactions, Quebec City, Canada, Jul. 19-23, 2009, 2 pages.
Borevitz et al., "Activation tagging identifies a conserved MYB regulator of phenylpropanoid biosynthesis," Plant Cell, 12:2383-2394, 2000.
Brown and Sachs, "Poly(A) tail length control in *Saccharomyces cerevisiae* occurs by message- specific deadenylation," Mol. Cell. Biol. 18(11):6548-6559, 1998.
Busk, "Regulatory elements in vivo in the promoter of the abscisic acid responsive gene rab 17 from maize," Plant J, 11:1285-1295, 1997.
Büttner and Bonas, "Getting across—bacterial type III effector proteins on their way to the plant cell," EMBO J, 2002, 21(20):5313-5322, 2002.
Büttner et al., "Functional analysis of HrpF, a putative type III translocon protein from Xanthomonas campestris pv. vesicatoria," J Bacteriol, 184(9):2389-2398, 2002.
Büttner et al., "HpaB from *Xanthomonas campestris* pv. vesicatoria acts as an exit control protein in type III-dependent protein secretion," Mol Microbiol, 54(3):755-768, 2004.
Büttner et al., "Targeting of two effector protein classes to the type III secretion system by a HpaC- and HpaB-dependent protein complex from Xanthomonas campestris pv. vesicatoria," Mol Microbiol, 59(2):513-527, 2006.
Canteros et al., "A gene from *Xanthomonas campestris* pv. vesicatoria that determines avirulence in tomato is related to avrBs3," Mol Plant Microbe Interact, 4(6):628-632, 1991.
Carlson et al., "Targeting DNA With Fingers and TALENs," Mol Ther Nucl Acids, 1:e3, doi:10.1038/mtna.2011.5, 4 pages, 2012.

Cathomen et al., "Zinc-finger nucleases: the next generation emerges," Mol Ther, 16(7):1200- 1207, 2008.
Cavalier et al., "Disrupting Two *Arabidopsis thaliana* Xylosyltransferase Genes Results in Plant Deficient in Xyloglucan, a Major Primary Cell Wall Component," The Plant Cell, 20:1519-1537 (Jun. 2008).
Cermak et al., "Efficient design and assembly of custom TALEN and other TAL effector-based constructs for DNA targeting," Nucleic Acids Res, 39:e82 (2011).
Cermak et al., Poster and Abstract—"Engineered TAL effector nucleases: new tools for genome editing," Northwest Genome Engineering Consortium Workshop on Genome Engineering, 3 pages, 2010.
Chen et al., "Characterization of an anther- and tapetum-specific gene and its highly specific promoter isolated from tomato," Plant Cell Rep., 25:231-240, 2006.
Chevalier et al., "Design, activity, and structure of a highly specific artificial endonuclease," Mol Cell, 10(4):895-905, 2002.
Choo et al., "In vivo repression by a site-specific DNA-binding protein designed against an oncogenic sequences," Nature, 372(6507):642-645, 1994.
Choulika et al., "Induction of homologous recombination in mammalian chromosomes by using.The I-SceI system of *Saccharomyces cerevisiae*," Mol Cell Biol, 15(4):1968-1973, 1995.
Christian et al., "Targeting DNA double-strand breaks with TAL effector nucleases," Genetics, 186:757-761 (2010).
Christian et al., Poster and Abstract—"Fusions of TAL effectors to the FokI endonuclease confer site specificity in DNA cleavage," IAPB 12th World Congress and In Vitro Biology Meeting, 4 pages, Jun. 2010.
Cole et al., "The Jpred 3 secondary structure prediction server," Nucl Acids Res, 36:W197-W201, 2008.
Cornelis, "The type III secretion injectisome," Nat Rev Microbiol, 4:811-825, 2006.
Curtin et al., "Targeted mutagenesis of duplicated genes in soybean with zinc-finger nucleases," Plant Physiology, 156(2):466-473 (2011).
De Feyter et al., "Gene-for genes interactions between cotton R genes and Xanthomonas campestris pv. malvacearum avr genes," Mol Plant Microbe Interact, 6(2):225-237, 1993.
De Pater et al., "bZIP proteins bind to a palindromic sequence without an ACGT core located in a seed-specific element of the pea lectin promoter," Plant J., 6:133-140, 1994.
Defrancesco, "Move over ZFNs," Nat Biotechnol, 29: 681-684, 2011.
Desjarlais and Berg, "Toward rules relating zinc finger protein sequences and DNA binding site preferences," Proc Natl Acad Sci USA, 89:7345-7349, 1992.
Domingues et al., "The Xanthomonas citri effector protein PthA interacts with citrus proteins involved in nuclear transport, protein folding and ubiquitination associated with DNA repair," Mol Plant Patho/, 11(5):663-675, DOI : 10.1111/ J .1364-3703.2010.00636.X, 13 pages, 2010.
Doyle et al., "TAL Effector-Nucleotide Targeter (TALE-NT) 2.0: tools for TAL effector design and target prediction," Nucleic Acids Res, 40:W117-122 (2012).
Draffehn et al., "Natural diversity of potato (*Solanum tuberosum*) invertases," BMC Plant Biol., 10:271, 15 pages (2010).
Durai et al., "Zinc finger nucleases: custom-designed molecular scissors for genome engineering of plant and mammalian cells," Nucl Acids Res, 33(1): 5978-5990, 2005.
Eisenschmidt et al., "Developing a programmed restriction endonuclease for highly specific DNA cleavage," Nucl Acids Res, 33:7039-7047, 2005.
Engler et al. "A One Pot, One Step, Precision Cloning Method with High Throughput Capability," PLoS One, 3: e3647, 7 pages, 2008.
Engler et al., "Golden Gate Shuffling: A One-Pot DNA Shuffling Method Based on Type IIs Restriction Enzymes," PLoS One, 4:e5553, 9 pages, 2009.
Fajardo-Sanchez et al., "Computer design of obligate heterodimer meganucleases allows efficient cutting of custom DNA sequences," Nucl Acids Res, 36(7):2163-2173, 2008.
Farran et al., "Targeted expression of human serum albumin to potato tubers," Transgenic Res., 11:337-346, 2002.

(56) References Cited

OTHER PUBLICATIONS

Foley et al., "Rapid Mutation of Endogenous Zebrafish Genes Using Zinc Finger Nucleases Made by Oligomerized Pool ENgineering (OPEN)," PLoS One, 13 pages, 4:e4348, 2009.
Fonfara et al., "Creating highly specific nucleases by fusion of active restriction endonucleases and catalytically inactive homing endonucleases," Nucl Acids Res, 40(2):847-860, 2011.
Fujikawa et al., "Suppression of defense response in plants by the avrBs3/pthA gene family of *Xanthomonas* spp," Mol Plant Microbe Interact, 19(3):342-349, 2006.
Gabriel et al., "An unbiased genome-wide analysis of zinc-finger nuclease specificity," Nat . Biotechnol, 29:816-823, 2011.
Geißler et al., "Transcriptional activators of human genes with programmable DNA-specificity," PLoS One, 6(5):e19509, May 2011.
GenBank Accession No. AAT46122, Nov. 12, 2004, 2 pages.
GenBank Accession No. ACD58243, May 19, 2008, 2 pages.
GenBank Accession No. AY986492, Jun. 24, 2005, 2 pages.
GenBank Accession No. CP000967, GI: 188518722, May 19, 2008, 606 pages.
GenBank Accession No. J04623, Apr. 26, 1993, 2 pages.
GenBank Accession No. M28828, Apr. 26, 1993, 3 pages.
GenBank Accession No. P14727, Jun. 28, 2011, 3 pages.
GenBank Accession No. X16130, Oct. 15, 2007, 3 pages.
Göhre and Robatzek, "Breaking the barriers: microbial effector molecules subvert plant immunity," Ann Rev Phytopathol, 46:189-215, 2008.
Gomez et al., "The pea END1 promoter drives anther-specific gene expression in different plant species," Planta, 219:967-981, 2004.
Gonchar et al., PspXI, a novel restriction endonuclease that recognizes the unusual DNA sequence 5'-VC↓TCGAGB-3', Bulletin of biotechnology and physico-chemical biology, 1(1):18-24, 2005, Translation by Ovchinnikov, "Science sibenzyme.com" [online], [retrieved on Aug. 11, 2011].Retrieved from the Internet: URL: <http://science.sibenzyme.com/article8_article_3_1.phtml>, 4 pages.
Gonzalez et al., "Molecular and pathotypic characterization of new Xanthomonas oryzae strains from West Africa," Mol Plant Microbe Interact, 20(5):534-546, 2007.
Govindarajulu et al., "Evaluation of constitutive viral promoters in transgenic soybean roots and nodules," Mol. Plant Microbe Interact, 21:1027-1035 (2008).
Greiner et al., "Ectopic expression of a tobacco invertase inhibitor homolog prevents cold-induced sweetening of potato tubers," Nature Biotechnology, 17(7):708-711 (1999).
Greisman and Pabo, "A general strategy for selecting high-affinity zinc finger proteins for diverse DNA target sites," Science, 275(5300):657-661, 1997.
Gu et al., "R gene expression induced by a type-III effector triggers disease resistance in rice," Nature, 435:1122-1125 (2005).
Gu et al., "Transcription activator-like type III effector AvrXa27 depends on OsTFIIAgamma5 for the activation of Xa27 transcription in rice that triggers disease resistance to Xanthomonas oryzae pv. oryzae," Mol Plant Pathol, 10(6):829-835, 2009.
Guan et al., "Heritable endogenous gene regulation in plants with designed polydactyl zinc finger transcription factors," Proc Natl Acad Sci USA, 99(20):13296-13301, 2002.
Gürlebeck et al., "Dimerization of the bacterial effector protein AvrBs3 in the plant cell cytoplasm prior to nuclear import," Plant J, 42:175-187, 2005.
Gürlebeck et al., "Type III effector proteins from the plant pathogen Xanthomonas and their role in the interaction with the host plant," J Plant Physiol, 163(3):233-255, 2006 (Epub 2005).
Gürlebeck et al., "Visualization of novel virulence activities of the Xanthomonas type III effectors AvrBsl, AvrBs3, and AvrBs4," Mol Plant Pathol, 10(2):175-188, 2009.
Haber, "In vivo biochemistry: Physical monitoring of recombination induced by site-specific endonucleases," Bioessays, 17:609-620, 1995.

Haberlach et al., "Isolation, culture and regeneration of protoplasts from potato and several related *Solanum* species," Plant Science, 39:67-74 (1985).
Hahn et al., "New mechanistic insights into the virulence activity of the Xanthomonas type III effector AvrBs3," (abstract), XIV International Congress on Molecular Plant-Microbe Interactions, Quebec City, Canada, Jul. 19-23, 2009, 2 pages.
Halford et al., "The reaction mechanism of FokI excludes the possibility of targeting zinc finger nucleases to unique DNA sites," Biochem Soc Trans, 39:584-588, 2011.
Handel et al., "Expanding or restricting the target site repertoire of zinc-finger nucleases: the inter-domain linker as a major determinant of target site selectivity," Mol Ther, 17:104-111, 2009.
Haun et al., "Improved soybean oil quality by targeted mutagenesis of fatty acid desaturase 2 gene family," Plant Biotechnology Journal, 1-7 (2014).
Herbers et al., "Race-specificity of plant resistance to bacterial spot disease determined by repetitive motifs in a bacterial avirulence protein," Nature, 356:172-174, 1992.
Heuer et al., "Repeat domain diversity of avrBs3-like genes in Ralstonia solanacearum strains and association with host preferences in the field," Appl Environ Microbiol, 73(13):4379-4384, 2007.
Hockemeyer et al., "Genetic engineering of human pluripotent cells using TALE nucleases," Nat Biotechnol, 29(8):731-734, 2011.
Hopkins et al., "Identification of a family of avirulence genes from Xanthomonas oryzae pv. oryzae," Mol Plant Microbe Interact, 5(6):451-459, 1992.
Hu et al., "Avirulence gene and insertion element-based RFLP as well as RAPD markers reveal high levels of genomic polymorphism in the rice pathogen Xanthomonas oryzae pv. oryzae," Syst Appl Microbiol, 30:587-600, 2007.
Huang et al., "Heritable gene targeting in zebrafish using customized TALENs," Nat Biotechnol, 29(8):699-700, 2011.
Hummel et al., "Rice gene activation by transcription activator-like effectors of Xanthomonas oryzae pvs. oryzae and oryzicola," poster presentation, and "A cipher-like mechanism governs TAL effector-DNA recognition," poster #13-517, XIV International Congress on Molecular Plant-Microbe Interactions, Quebec City, Canada, 3 pages, Jul. 19-23, 2009.
Hurt et al., "Highly specific zinc finger proteins obtained by directed domain shuffling and cell-based selection," Proc Natl Acad Sci USA, 100(21):12271-12276, 2003.
Isalan et al., "A rapid, generally applicable method to engineer zinc fingers illustrated by targeting the HIV-1 promoter," Nat Biotechnol, 19(7):656-660, 2001.
Jackel et al., "Protein design by directed devolution," Annu Rev Biophys, 37:155-173, 2008.
Jansen, "mRNA localization. message on the move," Nat. Rev. Mol. Cell Biol., 2:247-256, 2001.
Jones and Dangl, "The plant immune system," Nature, 444:323-329, 2006.
Jordan et al., "Physical delimitation of the pepper Bs3 resistance gene specifying recognition of the AvrBs3 protein from Xanthomonas campestris pv. vesicatoria," Theor Appl Genet, 113(5):895-905, 2006.
Kay and Bonas, "How Xanthomonas type III effectors manipulate the host plant," Curr Opin Microbiol, 12:37-43, 2009.
Kay et al., "A bacterial effector acts as a plant transcription factor and induces a cell size regulator," Science, 318:648-651 (2007).
Kay et al., "Characterization of AvrBs3-like effectors from a Brassicaceae pathogen reveals virulence and avirulence activities and a protein with a novel repeat architecture," Mol Plant Microbe Interact, 18(8):838-848, 2005.
Kay et al., "Detailed analysis of the DNA recognition motifs of the Xanthomonas type III effectors AvrBs3 and AvrBs3deltarep16," Plant J, 59(6):859-871, 2009.
Keshavarzi et al., "Basal defenses induced in pepper by lipopolysaccharides are suppressed by Xanthomonas campestris pv. vesicatoria," Mol Plant Microbe Interact, 17(7):805-815, 2004.
Kim and Chandrasegaran, "Chimeric restriction endonuclease," Proc Natl Acad Sci USA, 91(3):883-887 (Feb. 1994).

(56) References Cited

OTHER PUBLICATIONS

Kim et al., "Comparative analysis of three indigenous plasmids from Xanthomonas axonopodis pv. glycines," Plasmid, 56(2):79-87, 2006.
Kim et al., "Construction of a Z-DNA-specific restriction endonuclease," Proc Natl Acad Sci USA, 94(24):12875-12879, 1997.
Kim et al., "Hybrid restriction enzymes: zinc finger fusions to FokI cleavage," Proc Natl Acad Sci USA, 93:1156-1160, 1996.
Kim et al., "Site-specific cleavage of DNA-RNA hybrids by zinc finger/FokI cleavage domain fusions," Gene, 203(1):43-49, 1997.
Kim et al., "Targeted genome editing in human cells with zinc finger nucleases constructed via modular assembly," Genome Res, 19:1279-1288 (2009).
Knoop et al., "Expression of avirulence gene avrBs3 from Xanthomonas campestris pv. vesicatoria is not under the control of hrp genes and is independent of plant factors," J Bacteriol, 173(22):7142-7150, 1991.
Lahaye and Bonas, "Molecular secrets of bacterial type III effector proteins," Trends Plant Sci, 6(10):479-485, 2001.
Ledford, "Plant genes get fine tailoring," Nature News [online], Apr. 29, 2009 [retrieved on May 21, 2009]. Retrieved from the Internet: <URL: http://www.nature.com/news/2009/090429/full/news.2009.415 html>, 3 pages.
Lee et al., "Environmental Effects on Oleic Acid in Soybean Seed Oil of Plant Introductions with Elevated Oleic Concentration," Crop Science, 49:1762-1768 (Sep./Oct. 2009).
Li et al., "Functional domains in FokI restriction endonuclease," Proc Natl Acad Sci USA, 89(10):4275-4279, 1992.
Li et al., "Modularly assembled designed TAL effector nucleases for targeted gene knockout and gene replacement in eukaryotes," Nucl Acids Res, 39:6315-6325, 2011.
Li et al., "TAL nucleases (TALNs): hybrid proteins composed of TAL effectors and FokI DNA-cleavage domain," Nucleic Acids Research, 39(1):359-372, 2010.
Liang et al., "Cloning and characterization of a novel avirulence gene (arp3) from Xanthomonas oryzae pv. oryzae," DNA Seq, 15(2):110-117, 2004.
Liu et al., "Design of polydactyl zinc-finger proteins for unique addressing within complex genomes," Proc Natl Acad Sci USA, 94(11):5525-5530, 1997.
Livak and Schmittgen, "Analysis of relative gene expression data using real-time quantitative PCR and the 2(-Delta C(T)) Method," Method. Methods, 25:402-408 (2001).
Mahfouz et al., "De novo-engineered transcription activator-like effector (TALE) hybrid nuclease with novel DNA binding specificity creates double-strand breaks," Proc Natl Acad Sci USA, 108:2623-2628, 2011.
Mahfouz et al., "Tale nucleases and next generation GM crops," GM Crops, 2(2):99-103 (Apr. 2011).
Mak, "Sequence-specific DNA-binding TALEs," Nat Biotechnol, 29:43, 2011.
Marois et al., "The xanthomonas type III effector protein AvrBs3 modulates plant gene expression and induces cell hypertrophy in the susceptible host," Mol Plant Microbe Interact, 15(7):637-646, 2002.
Mehta et al., "Engineered polyamine accumulation in tomato enhances phytonutrient content, juice quality, and vine life," Nat. Biotechnol. 20:613-618, 2011.
Mignone et al., "Untranslated regions of mRNAs," Genome Biology, 3(3):reviews0004.1-0004.10, 10 pages, 2002.
Miller et al., "A TALE nuclease architecture for efficient genome editing," Nat Biotechnol, 29:143-148, 2011.
Miller et al., "An improved zinc-finger nuclease architecture for highly specific genome editing," Nature Biotechnol, 25:778-785, 2007.
Minczuk et al., "Development of a single-chain, quasi-dimeric zinc-finger nuclease for the selective degradation of mutated human mitochondrial DNA," Nucleic Acids Res, 36(12):3926-3938, 2008.
Mino et al., "Efficient double-stranded DNA cleavage by artificial zinc-finger nucleases composed of one zinc-finger protein and a single-chain FokI dimer," J Biotechnol, 140(3-4):156-161, 2009.

Moore et al., "Transactivated and chemically inducible gene expression in plants," Plant J, 45:651-683, 2006.
Morbitzer et al., "Assembly of custom Tale-type DNA binding domains by modular cloning," Nucleic Acids Research, 39(13):5790-5799, 2011.
Morbitzer et al., "Regulation of selected genome loci using de novo-engineered transcription activator-like effector (TALE)-type transcription factors," Proc Natl Acad Sci U S A., 107(50):21617-21622, 2010.
Moscou and Bogdanove, "A Simple Cipher Governs DNA Recognition by TAL Effectors," Science, 326(5959): 1501, 2009.
Muhlrad and Parker, "Mutations affecting stability and deadenylation of the yeast MFA2 transcript," Genes Dev., 6:2100-2111, 1992.
Murakami et al., "The repeat domain of the type III effector protein PthA shows a TPR-like structure and undergoes conformational changes upon DNA interaction," Proteins, 78:3386-3395, 2010.
Murray et al., "Rapid isolation of high molecular weight plant DNA," Nucl. Acids Res, 8(19):4321-4325 (1980).
Mussolino et al., "A novel TALE nuclease scaffold enables high genome editing activity in combination with low toxicity," Nucleic Acids Res, 39:9283-9293 (2011).
Nakagawa et al., "Development of series of gateway binary vectors, pGWBs, for realizing efficient construction of fusion genes for plant transformation," J Biosci Bioeng, 104:34-41, 2007.
Narsai et al., "Genome-wide analysis of mRNA decay rates and their determinants in Arabidopsis thaliana," Plant Cell, 19:3418-3436, 2007.
Niño-Liu et al., "Xanthomonas oryzae pathovars: model pathogens of a model crop," Mol Plant Pathol, 7(5):303-324, 2006.
Nissan et al. "The type III effectors HsvG and HsvB of gall-forming Pantoea agglomerans determine host specificity and function as transcriptional activators." Molecular Microbiology, 61(5): 1118-1131, 2006.
Noël et al., "XopC and XopJ, two novel type III effector proteins from Xanthomonas campestris pv. vesicatoria," J Bacteriol, 185(24):7092-7102, 2003.
Ovchinnikov et al., "PspXI, a novel restriction endonuclease that recognizes the unusual DNA sequence 5-VCTCGAGB-3," Bull Biotech Physio-Chemical Biol, 2005, 1(1):18-24, retrieved from the Internet: http://science.sibenzyme.com/article8_article_3_1.phtml.
Padidam, "Chemically regulated gene expression in plants," Curr Opin Plant Biol, 6:169-177, 2003.
Paques and Duchateau, "Meganucleases and DNA Double-Strand Break-Induced recombination: Perspectives for Gene Therapy," Curr Gene Ther, 7:49-66, 2007.
Park et al., "Avirulence gene diversity of Xanthomonas axonopodis pv. Glycines isolated in Korea," J Microbiol Biotechnol, 18(9):1500-1509, 2008.
Pattanayak et al., "Revealing off-target cleavage specificities of zinc-finger nucleases by in vitro selection," Nat Methods, 8:765-770, 2011.
Paulus et al., "Silencing β1,2-xylosyltransferase in transgenic tomato fruits reveals xylose as constitutive component in IgE-binding epitopes," Frontiers in Plant Science, 2(42), 12 pages (Aug. 2011).
Pavletich and Pabo, "Zinc finger-DNA recognition: crystal structure of a Zif268-DNA complex at 2.1 A," Science, 252:809-817, 1991.
Pearson, "The fate of fingers," Nature, 455:160-164, 2008.
Pennisi, "The Tale of the TALES," Science, 338(6113):1408-1411, 2012.
Pesole et al., "Structural and functional features of eukaryotic mRNA untranslated regions," Gene, 276: 73-81, 2001.
Pham et al., "Mutant alleles of FAD2-1A and FAD2-1B combine to produce soybeans with the high oleic acid seed oil trait," BMC Plant Biol., 10:195 (2010).
Pingoud and Silva, "Precision genome surgery," Nature Biotechnol, 25(7):743-744, 2007.
Podhajska and Szybalski, "Conversion of the FokI endonuclease to a universal restriction enzyme: cleavage of phage M13mp7 DNA at predetermined sites," Gene, 40(2-3):175-182, 1985.
Pomerantz et al., "Structure-based design of transcription factors," Science, 267(5194):93-96, 1995.
Porteus and Baltimore, "Chimeric nucleases stimulate gene targeting in human cells," Science, 300:763, 2003.

(56) References Cited

OTHER PUBLICATIONS

Porteus and Carroll, "Gene targeting using zinc finger nucleases," Nature Biotechnol, 23:967-973, 2005.
Porteus, "Zinc fingers on target," Nature, 459: 337-338, 2009.
Potenza et al., "Targeting transgene expression in research, agricultural, and environmental applications: Promoters used in plant transformation," In vitro Cell Dev Biol, 40(1):1-22, 2004.
Puchta et al., "Homologous recombination in plant cells is enhanced by in vivo induction of double strand breaks into DNA by a site-specific endonuclease," Nucl Acids Res, 21(22):5034-5040, 1993.
Radecke et al., "Zinc-finger nuclease-induced gene repair with oligodeoxynucleotides: wanted and unwanted target locus modifications," Mol Ther, 18(4):743-753, 2010.
Reyon et al., "FLASH assembly of TALENs for high-throughput genome editing," Nat Biotechnol, 30:460-465 (2012).
Römer et al., "Plant pathogen recognition mediated by promoter activation of the pepper Bs3 resistance gene," Science, 318(5850):645-648 (2007).
Römer et al., "A single plant resistance gene promoter engineered to recognize multiple TAL effectors from disparate pathogens," Proc Natl Acad Sci USA, 106(48):20526-31, 2009.
Römer et al., "Promoter elements of rice susceptibility genes are bound and activated by specific TAL effectors from the bacterial blight pathogen, Xanthomonas oryzae pv. oryzae," New Phytol, 187:1048-1057, 2010.
Römer et al., "Recognition of AvrBs3-Like Proteins is Mediated by Specific Binding to Promoters of Matching Pepper Bs3 Alleles," Plant Physiol, 150:1697-1712, 2009.
Romero et al., "Temperature Sensitivity of the Hypersensitive Response of Bell Pepper to Xanthomonas axonopodis pv. vesicatoria," Phytopathology, 92(2):197-203, 2002.
Rossier et al., "HrpB2 and HrpF from Xanthomonas are type III-secreted proteins and essential for pathogenicity and recognition by the host plant," Mol Microbiol, 38(4):828-838, 2000.
Rossier et al., "The Xanthomonas Hrp type III system secretes proteins from plant and mammalian bacterial pathogens," Proc Natl Acad Sci USA, 96(16):9368-9373, 1999.
Rouet et al., "Expression of a site-specific endonuclease stimulates homologous recombination in mammalian cells," Proc Natl Acad Sci USA, 91(13):6064-6068, 1994.
Rouet et al., "Introduction of double-strand breaks into the genome of mouse cells by expression of a rare-cutting endonuclease," Mol Cell Biol, 14(12):8096-8106, 1994.
Rybak et al., "Identification of *Xanthomonas citri* ssp. citri host specificity genes in a heterologous expression host," Mol Plant Pathol, 10(2):249-262, 2009.
Sandhu et al., "Enhanced oleic acid content in the soybean mutant M23 is associated with the deletion in the Fad2-la gene encoding a fatty acid desaturase," JAOCS, 84:229-235, 2007.
Santiago et al., "Targeted gene knockout in mammalian cells by using engineered zinc-finger nucleases," Proc Natl Acad Sci USA, 105(15):5809-5814, 2008.
Scholze and Boch, "TAL effectors are remote controls for gene activation," Curr Opin Microbiol, 14:47-53, 2011.
Scholze and Boch. "TAL effector-DNA specificity," Virulence, 1(5):428-432, 2010.
Schornack et al., "Characterization of AvrHah1, a novel AvrBs3-like effector from Xanthomonas gardneri with virulence and avirulence activity," New Phytol, 179:546-556, 2008.
Schornack et al., "Expression levels of avrBs3-like genes affect recognition specificity in tomato Bs4—but not in pepper BS3-mediated perception," Mol Plant-Microbe Interact, 18(11):1215-1225, 2005.
Schornack et al., "Gene-for-gene-mediated recognition of nuclear-targeted AvrBs3-like bacterial effector proteins," J. Plant Physiol, 163:256-272 (2006).
Schornack et al., "The tomato resistance protein Bs4 is a predicted non-nuclear TIR-NB-LRR protein that mediates defense responses to severely truncated derivatives of AvrBs4 and overexpressed AvrBs3," Plant J, 37(1):46-60, 2004.
Segal et al., "Endonuclease-induced, targeted homologous extrachromosomal recombination in Xenopus oocytes," Proc Natl Acad Sci USA, 92(3):806-810, 1995.
Sera, "Inhibition of virus DNA replication by artificial zinc finger proteins," J Virol, 79(4):2614-2619, 2005.
Shepard and Totten, "Mesophyll cell protoplasts of potato: isolation, proliferation, and plant regeneration," Plant Physiol., 60:313-316(1977).
Shukla et al., "Precise genome modification in the crop species *Zea mays* using zinc-finger nucleases," Nature, 459(7245):437-441, 2009.
Simon et al., "Targeting DNA with triplex-forming oligonucleotides to modify gene sequence," Biochimie, 90:1109-1116, 2008.
Skipper, "Technology: The holy grail for plant biologists," Nature Reviews Genetics, 10(6):350, 2009.
Stoddard et al., "Creation of high oleic soybean oil via targeted mutagenesis of FAD2 gene family," ISB News Report, 4 pages, 2014.
Strasser et al., "Generation of glycol-engineered *Nicotiana benthamiana* for the production of monoclonal antibodies with a homogeneous human-like N-glycan structure," Plant Biotechnology Journal, 6:392-402 (2008).
Studholme et al., "Genome-wide sequencing data reveals virulence factors implicated in banana Xanthomonas wilt," FEMS Microbiol Lett, 310(2):182-192, 2010.
Sugio et al., "Two type III effector genes of Xanthomonas oryzae pv. oryzae control the induction of the host genes OsTFIIAgamma1 and OsTFX1 during bacterial blight of rice," Proc Natl Acad Sci USA, 104:10720-10725 (2007).
Swarup et al., "An Xanthomonas citri pathogenicity gene, pthA, pleiotropically encodes gratuitous avirulence on nonhosts," Mol Plant Microbe Interact, 5(3):204-213, 1992.
Szurek et al. "Type III-dependent translocation of the Xanthomonas AvrBs3 protein into the plant cell," Mol Microbiol, 46(1): 13-23, 2002.
Szurek et al., "Eukaryotic features of the Xanthomonas type III effector AvrBs3: protein domains involved in transcriptional activation and the interaction with nuclear import receptors from pepper," Plant J, 26(5):523-534, 2001.
Takenaka et al., "Inhibition of tomato yellow leaf curl virus replication by artificial zinc-finger proteins," Nucl Acids Symposium Series, 51(1):429-430, 2007.
Thieme et al., "New type III effectors from Xanthomonas campestris pv. vesicatoria trigger plant reactions dependent on a conserved N-myristoylation motif," Mol Plant Microbe Interact, 20(10):1250-1261, 2007.
Thierry et al., "Cleavage of yeast and bacteriophage T7 genomes at a single site using the rare cutter endonuclease I-Sce I," Nucl Acids Res, 19(1):189-190, 1991.
Tovkach et al., "A toolbox and procedural notes for characterizing novel zinc finger nucleases for genome editing in plant cells," Plant J, 57:747-757, 2009.
Townsend et al., "High-frequency modification of plant genes using engineered zinc-finger nucleases," Nature, 459:442-445, 2009.
Urnov et al., "Highly efficient endogenous human gene correction using designed zinc-finger nuclease," Nature, 435(7042):646-651, 2005.
Van Den Ackerveken et al., "Recognition of the bacterial avirulence protein AvrBs3 occurs inside the host plant cell," Cell, 87(7):1307-1316, 1996.
Van Den Elzen et al., "A chimaeric hygromycin resistance gene as a selectable marker in plant cells," Plant Molecular Biology, 5:299-302 (1985).
Van Der Velden and Thomas, "The role of the 5' untranslated region of an mRNA in translation regulation during development," Int. J. Biochem. Cell Biol., 31:87-106, 1999.
Vaughan et al., "Characterization of FaRB7, a near root-specific gene from strawberry (*Fragariaxananassa duch.*) and promoter activity analysis in homologous and heterologous hosts," J. Exp. Botany, 57:3901-3910, 2006.

(56) References Cited

OTHER PUBLICATIONS

Vergunst et al., "VirB/D4-Dependent Protein Translocation from Agrobacterium into Plant Cells," Science, 290:979-982, 2000.
Voytas et al., "Plant science. DNA binding made easy," Science, 326(5959):1491-1492, 2009.
Wah et al., "Structure of FokI has implications for DNA cleavage," Proc Natl Acad Sci USA, 95(18):10564-10569, 1998.
Wah et al., "Structure of the multimodular endonuclease FokI bound to DNA," Nature, 388(3):97- 100, 1997.
Wang et al., "Chemically regulated expression systems and their applications in transgenic plants," Transgenic Res, 12:529-540, 2003.
Weber et al., "The type III-dependent Hrp pilus is required for productive interaction of Xanthomonas campestris pv. vesicatoria with pepper host plants," J Bacteriol, 187(7):2458-2468, 2005.
White and Yang, "Host and pathogen factors controlling the rice/Xanthomonas oryzae interaction," Plant Physiol, 150:1677-1686, 2009.
White et al., "The type III effectors of Xanthomonas," Mol Plant Pathol, 10:749-766, 2009.
Wright et al., "High-frequency homologous recombination in plants mediated by zinc-finger nucleases," Plant J, 44:693-705 (2005).
Yang and White, "Diverse members of the AvrBs3/PthA family of type III effectors are major virulence determinants in bacterial blight disease of rice," Mol Plant Microbe Interact, 17(11):1192-1200, 2004.
Yang et al. "The virulence factor AvrXa7 of Xanthomonas oryzae of Oryzae is a type III secretion pathway-dependent nuclear-localized double stranded DNA binding protein," Proc Natl Acad Sci USA, 97(17): 9807-9812, 2000.
Yang et al., "Avoidance of host recognition by alterations in the repetitive and C-terminal regions of AvrXa7, a type III effector of Xanthomonas oryzae pv. oryzae," Mol Plant Microbe Interact, 18(2):142-149, 2005.
Yang et al., "Os8N3 is a host disease-susceptibility gene for bacterial blight of rice," Proc Natl Acad Sci USA, 103:10503-10508 (2006).
Yoo et al., "*Arabidopsis mesophyll* protoplasts: a versatile cell system for transient gene expression analysis," Nature Protocols, 2:1565-1572 (2007).
Yuan et al., "Characterization of Xanthomonas oryzae-responsive cis-acting element in the promoter of rice race-specific susceptibility gene Xa13," Mol Plant, 4(2):300-309, 2011.
Zetsche et al., "Cpf1 is a single RNA-guided endonuclease of a class 2 CRISPR-Cas system," Cell, 163:759-771, 2015.
Zhang et al., "Efficient construction of sequence-specific TAL effectors for modulating mammalian transcription.," Nat Biotechnol, 29:149-153 (2011).
Zhang et al., "High frequency targeted mutagenesis in *Arabidopsis thaliana* using zinc finger nucleases," Proc Natl Acad Sci USA, 107(26):12028-12033 (2010).
Zhang et al., "RNAi effects on regulation of endogenous acid invertase activity in potato (*Solanum tuberosum* L.) tubers," Chin J Agric. Biotechnol, 5:107-111 (2008).
Zhu et al., "The C terminus of AvrXa10 can be replaced by the transcriptional activation domain of VP16 from the herpes simplex virus," Plant Cell, 11(9):1665-1674, 1999.
Zhu et al., "AvrXa10 Contains an Acidic Transcriptional Activation Domain in the Functionally Conserved C Terminus," Molecular Plant-Microbe Interactions, 11(8): 824-832, 1998.
Zhu et al., "The rsmA-like gene rsmA(XOO) of Xanthomonas oryzae pv. oryzae regulates bacterial virulence and production of diffusible signal factor," Mol Plant Pathol, 12(3):227-237, 2011, Epub 2010.
Zou et al., "Identification of an avirulence gene, avrxa5, from the rice pathogen Xanthomonas oryzae pv. oryzae," Sci China Life Sci, 53(12):1440-1449, 2010.
Zrenner et al., "Soluble acid invertase determines the hexose-to sucrose ratio in cold-stored potato tubers," *Planta*, 198(2):246-252 (1996).
Zuo and Chua, "Chemical-inducible systems for regulated expression of plant genes," Curr Opin Biotechnol, 11:146-151, 2000.
Zuo et al., "Technical advance: An estrogen receptor-based transactivator XVE mediates highly inducible gene expression in transgenic plants," Plant J. 24:265-273 (2000).
Vandesompele et al., "Accurate normalization of real-time quantitative RT-PCR data by geometric averaging of multiple internal control genes," Genome Biology; 2002, 3(7):research0034.1-0034.11.

\* cited by examiner

FIG. 1

ALS2_T1

GCTTTGCTCATCGTCACTGTTGTACTATTAAGTAGTTGATATTTATGTTTGTTTTGCATCATCCCCTTTGGTTTTGAATGTG
AAGGATTTCAGCAAAGTTCATCCTCTATTTGCAACAATCTGGAGATTAATTCTAATGAGTAGTTTAGTGTAATAAAGTTA
GCTTGTTCCACATTTTATTTCATAAGCTATGTCATGCTGGGTCAGATTGGAACTTCCTCTTTAGGTTGGATGTAATCCCTAT
TAGG (SEQ ID NO: 1)

FIG. 5

| Sequence | Number of Deletions | SEQ ID NO: # |
|---|---|---|
| TAGCTTGTTCCACATTTTTATTTCATAAGCTATGTCATGCTGGGTCAG | 0 | 4 |
| TAGCTTGTTCCACATTTT------TAAGCTATGTCATGCTGGGTCAG | 7 | 5 |
| TAGCTTGTTCCACATTTT--------------TGTCATGCTGGGTCAG | 14 | 6 |
| TAGCTTGTTCCACATTTTTAT-------GCTATGTCATGCTGGGTCAG | 7 | 7 |
| TAGCTTGTTCCACATTTTTATTT----AGCTATGTCATGCTGGGTCAG | 4 | 8 |

FIG. 6

| Sequence | Number of Deletions | SEQ ID NO: # |
|---|---|---|
| TTAGCTTGTTCCACATTTTTTATTTCATAAGCTATGTCATGCTGGGTCAGA | 0 | 4 |
| TTAGCTTGTTCCACATTTTTTATTT--TAAGCTATGTCATGCTGGGTCAGA | -2 | 18 |
| TTAGCTTGTTCCACATTTTTTATT---TAAGCTATGTCATGCTGGGTCAGA | -3 | 19 |
| TTAGCTTGTTCCACATTTTTTATTT----AGCTATGTCATGCTGGGTCAGA | -4 | 8 |
| TTAGCTTGTTCCACATTTTTT-----ATAAGCTATGTCATGCTGGGTCAGA | -5 | 20 |
| TTAGCTTGTTCCACATTTTT------TAAGCTATGTCATGCTGGGTCAGA | -7 | 5 |
| TTAGCTTGTTCCACATTTTTTAT-------GCTATGTCATGCTGGGTCAGA | -7 | 7 |
| TTAGCTTGTTCCACATTTTTTATT--------TATGTCATGCTGGGTCAGA | -8 | 21 |
| TTAGCTTGTTCCACATTTT----------TATGTCATGCTGGGTCAGA | -12 | 22 |
| TTAGCTTGTTCCACATTTT------------TGTCATGCTGGGTCAGA | -14 | 6 |
| TT--------------------------AGCTATGTCATGCTGGGTCAGA | -26 | 23 |

MODIFYING MESSENGER RNA STABILITY IN PLANT TRANSFORMATIONS

CROSS-REFERENCE TO RELATED APPLICATIONS

This application claims benefit of priority from U.S. Provisional Application Ser. No. 62/219,842, filed on Sep. 17, 2015.

TECHNICAL FIELD

This document relates to materials and methods for genome engineering through transient expression of a targeted nuclease. The methods can include, for example, modifying the stability of messenger RNA (mRNA) encoding the nuclease by the addition of untranslated regions (UTRs).

BACKGROUND

Gene expression, the process of converting information from DNA to protein, is regulated by the non-coding portions of the genome, (e.g., promoters, enhancers, locus control regions and silencers), by transcription factors, and by post-transcriptional mechanisms. The stability and level of mRNA are extremely important in gene expression. Post-transcriptional control of mRNA nucleo-cytoplasmic transport, translational efficiency, subcellular localization and stability are known to be mediated by cis-acting RNA elements located in the 5' and 3' mRNA UTRs (Pesole et al., *Gene* 276: 73-81, 2001; and Mignone et al., *Genome Biology* 3(3):reviews0004.1-0004.10, 2002).

SUMMARY

Genome editing via mRNA can be desirable due to its non-transgenic nature. However, mRNA is a fragile molecule that is susceptible to degradation during the plant transformation process, and it may be quickly degraded before translation can reach an acceptable level for an expressed polypeptide to have an effect. The present document is based at least in part on the discovery that utilization of certain UTRs in mRNA plant transformations allow for increased stability, localization, and translational efficiency of mRNA molecules. For example, by including one or more particular UTRs in an mRNA transcript, it is possible to increase transient expression of the encoded protein(s). In some cases, therefore, methods for genome editing can include the use of an mRNA expression vector as described herein, to produce nuclease transcripts that are more stable and thus better able to transiently express sequence-specific nucleases capable of site-directed genome modification, enabling enhanced engineering of plant species.

In one aspect, this document features a nucleic acid comprising (a) a structural coding sequence encoding a rare-cutting endonuclease or a rare-cutting endonuclease subunit, and (b) a 5' untranslated region (UTR), a 3' UTR, or both a 5' UTR and a 3' UTR, wherein the 5' UTR, 3' UTR, or 5' UTR and 3' UTR are operably linked to the structural coding sequence.

The 5' UTR can contain the nucleic acid sequence set forth in SEQ ID NO:10, or a nucleic acid sequence having at least 95 percent identity to SEQ ID NO:10. The 3' UTR can contain the nucleic acid sequence set forth in SEQ ID NO:11, or a nucleic acid sequence having at least 95 percent identity to SEQ ID NO:11. In some cases, the 5' UTR can contain the nucleic acid sequence set forth in SEQ ID NO:10, or a nucleic acid sequence having at least 95 percent identity to SEQ ID NO:10, and the 3' UTR can contain the nucleic acid sequence set forth in SEQ ID NO:11, or a nucleic acid sequence having at least 95 percent identity to SEQ ID NO:11.

The 5' UTR can contain the nucleic acid sequence set forth in SEQ ID NO:12, or a nucleic acid sequence having at least 95 percent identity to SEQ ID NO:12. The 3' UTR can contain the nucleic acid sequence set forth in SEQ ID NO:13, or a nucleic acid sequence having at least 95 percent identity to SEQ ID NO:13. In some cases, the 5' UTR can contain the nucleic acid sequence set forth in SEQ ID NO:12, or a nucleic acid sequence having at least 95 percent identity to SEQ ID NO:12, and the 3' UTR comprises the nucleic acid sequence set forth in SEQ ID NO:13, or a nucleic acid sequence having at least 95 percent identity to SEQ ID NO:13.

The 5' UTR can contain the nucleic acid sequence set forth in SEQ ID NO:14, or a nucleic acid sequence having at least 95 percent identity to SEQ ID NO:14. The 3' UTR can contain the nucleic acid sequence set forth in SEQ ID NO:15, or a nucleic acid sequence having at least 95 percent identity to SEQ ID NO:15 In some cases, the 5' UTR can contain the nucleic acid sequence set forth in SEQ ID NO:14, or a nucleic acid sequence having at least 95 percent identity to SEQ ID NO:14, and the 3' UTR can contain the nucleic acid sequence set forth in SEQ ID NO:15, or a nucleic acid sequence having at least 95 percent identity to SEQ ID NO:15.

The 5' UTR can contain the nucleic acid sequence set forth in SEQ ID NO:16, or a nucleic acid sequence having at least 95 percent identity to SEQ ID NO:16. The 3' UTR can contain the nucleic acid sequence set forth in SEQ ID NO:17, or a nucleic acid sequence having at least 95 percent identity to SEQ ID NO:17. In some cases, the 5' UTR can contain the nucleic acid sequence set forth in SEQ ID NO:16, or a nucleic acid sequence having at least 95 percent identity to SEQ ID NO:16, and the 3' UTR can contain the nucleic acid sequence set forth in SEQ ID NO:17, or a nucleic acid sequence having at least 95 percent identity to SEQ ID NO:17.

The rare-cutting endonuclease can be a transcription activator-like effector-endonuclease, a zinc-finger nuclease, a meganuclease, or a programmable RNA-guided endonuclease. The nucleic acid can further include a promoter operably linked to the structural coding sequence. The nucleic acid of claim 1, wherein the nucleic acid can be a messenger RNA (mRNA) or a DNA.

In another aspect, this document features an expression vector containing a nucleic acid as described herein.

In another aspect, this document features a method for synthesizing an expression vector. In some embodiments, the method can include operably linking together (a) a promoter sequence, (b) a structural coding sequence, and (c) a 5' UTR nucleic acid sequence having at least 90% identity with SEQ ID NO:10, SEQ ID NO:12, SEQ ID NO:14, or SEQ ID NO:16. In some embodiments, the method can include operably linking together (a) a promoter sequence, (b) a structural coding sequence, and (c) a 3' UTR nucleic acid sequence having at least 90% identity with SEQ ID NO:11, SEQ ID NO:13, SEQ ID NO:15, or SEQ ID NO:17.

This document also features a method for modifying the genomic material of a plant, plant part, or plant cell. The method can include introducing into the plant, plant part, or plant cell a nucleic acid comprising (a) a structural coding sequence encoding a rare-cutting endonuclease or a rare-cutting endonuclease subunit targeted to a genomic sequence within the plant cell, and (b) a 5' untranslated region (UTR), a 3' UTR, or both a 5' UTR and a 3' UTR, wherein the 5' UTR, 3' UTR, or 5' UTR and 3' UTR are operably linked to the structural coding sequence.

The 5' UTR can contain the nucleic acid sequence set forth in SEQ ID NO:10, or a nucleic acid sequence having at least 95 percent identity to SEQ ID NO:10. The 3' UTR can contain the nucleic acid sequence set forth in SEQ ID NO:11, or a nucleic acid sequence having at least 95 percent identity to SEQ ID NO:11. In some cases, the 5' UTR can contain the nucleic acid sequence set forth in SEQ ID NO:10, or a nucleic acid sequence having at least 95 percent identity to SEQ ID NO:10, and the 3' UTR can contain the nucleic acid sequence set forth in SEQ ID NO:11, or a nucleic acid sequence having at least 95 percent identity to SEQ ID NO:11.

The 5' UTR can contain the nucleic acid sequence set forth in SEQ ID NO:12, or a nucleic acid sequence having at least 95 percent identity to SEQ ID NO:12. The 3' UTR can contain the nucleic acid sequence set forth in SEQ ID NO:13, or a nucleic acid sequence having at least 95 percent identity to SEQ ID NO:13. In some cases, the 5' UTR can contain the nucleic acid sequence set forth in SEQ ID NO:12, or a nucleic acid sequence having at least 95 percent identity to SEQ ID NO:12, and the 3' UTR can contain the nucleic acid sequence set forth in SEQ ID NO:13, or a nucleic acid sequence having at least 95 percent identity to SEQ ID NO:13.

The 5' UTR can contain the nucleic acid sequence set forth in SEQ ID NO:14, or a nucleic acid sequence having at least 95 percent identity to SEQ ID NO:14. The 3' UTR can contain the nucleic acid sequence set forth in SEQ ID NO:15, or a nucleic acid sequence having at least 95 percent identity to SEQ ID NO:15. In some cases, the 5' UTR can contain the nucleic acid sequence set forth in SEQ ID NO:14, or a nucleic acid sequence having at least 95 percent identity to SEQ ID NO:14, and the 3' UTR can contain the nucleic acid sequence set forth in SEQ ID NO:15, or a nucleic acid sequence having at least 95 percent identity to SEQ ID NO:15.

The 5' UTR can contain the nucleic acid sequence set forth in SEQ ID NO:16, or a nucleic acid sequence having at least 95 percent identity to SEQ ID NO:16. The 3' UTR can contain the nucleic acid sequence set forth in SEQ ID NO:17, or a nucleic acid sequence having at least 95 percent identity to SEQ ID NO:17. In some cases, the 5' UTR can contain the nucleic acid sequence set forth in SEQ ID NO:16, or a nucleic acid sequence having at least 95 percent identity to SEQ ID NO:16, and the 3' UTR can contain the nucleic acid sequence set forth in SEQ ID NO:17, or a nucleic acid sequence having at least 95 percent identity to SEQ ID NO:17.

The rare-cutting endonuclease can be a transcription activator-like effector-endonuclease, a zinc-finger nuclease, a meganuclease, or a programmable RNA-guided endonuclease. The nucleic acid can further include a promoter operably linked to the structural coding sequence. The plant, plant part, or plant cell can be a dicotyledonous plant, plant part, or plant cell (e.g., a dicotyledonous plant, plant part, or plant cell from the family Brassicaceae, Solanaceae, Fabaceae, or Roseacaeae). The plant, plant part, or plant cell can be a monocotyledous plant, plant part, or plant cell (e.g., a monocotyledonous plant, plant part, or plant cell from the family Poaceae or Liliaceae). The nucleic acid can be an mRNA, and in some cases, introducing can include polyethylene glycol- (PEG-) mediated transformation, electroporation-mediated transformation, or biolistics-mediated transformation of the nucleic acid. The nucleic acid can be a DNA, and in some cases, the introducing can include PEG-mediated transformation, electroporation-mediated transformation, biolistics-mediated transformation, or *Agrobacterium*-mediated transformation of the nucleic acid. The rare-cutting endonuclease can be a transcription activator-like effector-endonuclease, a zinc-finger nuclease, a meganuclease, or a programmable RNA-guided endonuclease. Transient expression of the rare-cutting endonuclease or rare-cutting endonuclease subunit can result in site-directed mutagenesis at the targeted sequence. The method can further include regenerating the plant cell or plant part into a plant.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows a representative DNA sequence (SEQ ID NO:1) from the ALS2 gene. The underlined sequences (SEQ ID NOS:2 and 3) represent target sites for transcription activator-like effector-nucleases (TALE-nucleases) that recognize the ALS2 gene.

FIG. 5 shows examples of TALE-nuclease-induced mutations in the ALS2 gene. The top line shows unmodified DNA sequence, with the sequences of recognition sites for the ALS2 TALE-nucleases underlined. The other sequences show representative mutations that were induced by imprecise non-homologous end joining (NHEJ). Deletion sizes are given at the right.

FIG. 6 shows additional examples of TALE-nuclease-induced mutations in the ALS2 gene after delivery of mRNA harboring the At1G09740 UTR pair.

DETAILED DESCRIPTION

Figure 2:
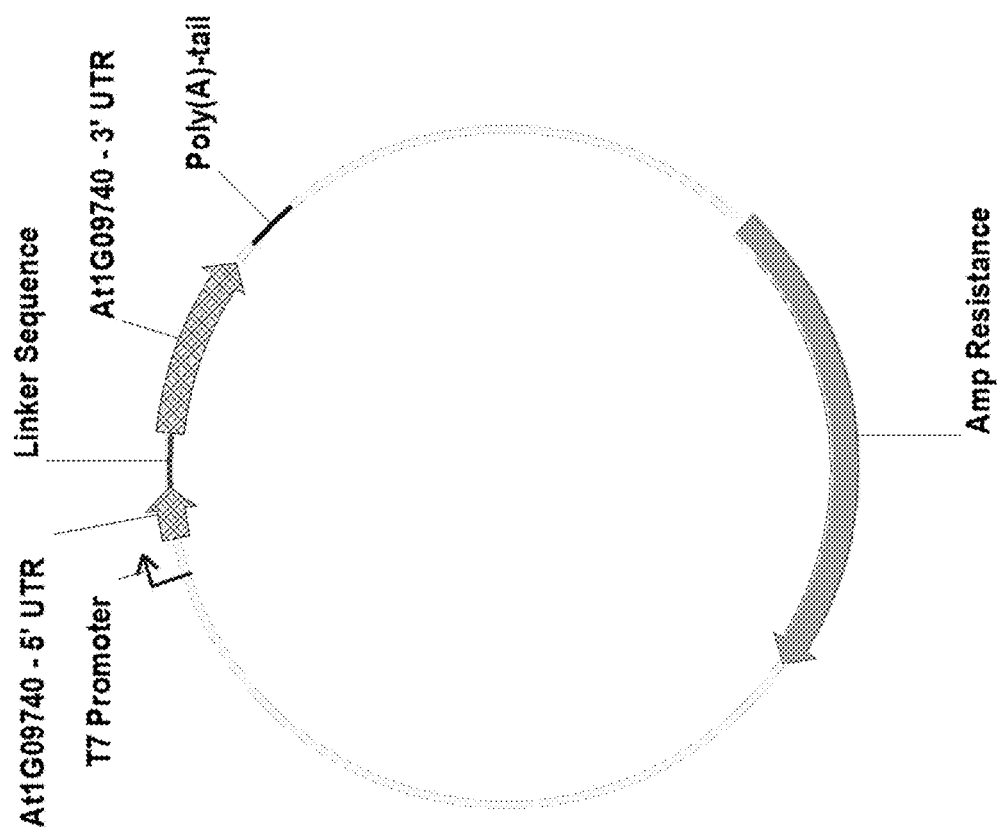
FIG. 2 is a diagram of a modified pSP72 vector containing the At1G09740 5' and 3' UTRs.

The global demand for food quantity and quality is ever increasing. To accommodate these growing needs, several genome engineering strategies have been employed to obtain crops at a rate faster than traditional breeding can provide. Genetic engineering offers a route to develop novel plant varieties that are able to thrive under environmental and agricultural constraints, optimizing the energy returned on investment. The vast majority of genetically engineered (GE) crops have traits, such as herbicide and pesticide resistance, that were introduced using transgenic methods. While effective, such methods typically involve insertion of foreign genetic material, and transgenic strains therefore typically require long and arduous regulatory steps before public use is approved (Stoddard et al., *ISB Newsletter*, 2014). In contrast, the methods described herein involve the transient expression of desired polypeptides by delivery of mRNA transcripts. The transformation of plants, plant parts, or plant cells with mRNA can be particularly useful, since mRNA is not capable of being inserted into plant genomes. Thus, the methods set forth herein can provide tools that are capable of producing novel crops without integration of foreign nucleic acids, which reduces the large scale screenings that would otherwise be necessary to identify a GE plant without the inadvertent incorporation of plasmid DNA.

In eukaryotes, mature mRNAs have a tripartite structure made up of a 5' UTR, a coding region, and a 3' UTR. The UTRs can play a major role in post-transcriptional translation efficiency (van der Velden, *Int. J. Biochem. Cell Biol.* 31:87-106, 1999), subcellular localization (Jansen, *Nat. Rev. Mol. Cell Biol.* 2:247-256, 2001) and stability (Bashirullah et al., *Proc. Natl. Acad. Sci. USA* 98(13):7025-7028, 2001) of the mRNA. mRNA stability can be essential for regulation of gene expression, as the half-life of the mRNA can affect the amount of the corresponding protein that is produced. In some cases, cis-acting elements in the 3' UTR, such as AU-rich elements (AREs), are capable of modulating the stability and translation efficiency of mRNA transcripts (Muhlrad, et al., *Genes Dev.* 6:2100-2111, 1992; Brown et al., *Mol. Cell. Biol.* 18(11):6548-6559, 1998). It is to be noted that in some cases, for example, these elements can induce rapid decay of the corresponding transcripts. A reduction in mRNA stability and translation efficiency may be useful in applications where it would be detrimental to have highly targeted mutagenesis by a rare-cutting endonuclease (e.g., disruption of a single copy of a gene).

As described herein, the ability of UTRs to increase or decrease transcript half-life can provide novel methods for introducing mRNA into plants, plant parts, or plant cells. When the mRNA encodes a rare-cutting endonuclease targeted to a particular sequence within a plant, an increased half-life can lead to an increased level of genome engineering at the desired target sequence.

As used herein, the terms "plant" and "plant part" refer to cells, tissues, organs, seeds, and severed parts (e.g., roots, leaves, and flowers) that retain the distinguishing characteristics of the parent plant. "Seed" refers to any plant structure that is formed by continued differentiation of the ovule of the plant, following its normal maturation point at flower opening, irrespective of whether it is formed in the presence or absence of fertilization and irrespective of whether or not the seed structure is fertile or infertile.

"Mutagenesis" as used herein refers to processes in which mutations are introduced into a selected DNA sequence. Mutations induced by endonucleases generally are obtained by a double-strand break, which results in insertion/deletion mutations ("indels") that can be detected by deep-sequencing analysis. Such mutations typically are deletions of several base pairs, and have the effect of inactivating the mutated allele. In the methods described herein, for example, mutagenesis occurs via double-stranded DNA breaks made by nucleases targeted to selected DNA sequences in a plant cell. Such mutagenesis results in "nuclease-induced mutations" (e.g., nuclease-induced knockouts, such as TALE-nuclease-induced knockouts) and reduced expression of the targeted gene. Following mutagenesis, plants can be regenerated from the treated cells using known techniques (e.g., planting seeds in accordance with conventional growing procedures, followed by self-pollination).

The term "expression" as used herein refers to the transcription of a particular nucleic acid sequence to produce sense or antisense RNA or mRNA, and/or the translation of an mRNA molecule to produce a polypeptide, with or without subsequent post-translational events.

The term "modulating" as used herein refers to increasing or decreasing translational efficiency of an mRNA. This can be accomplished by inserting, removing, or altering a 5' UTR sequence, a 3' UTR sequence, or 5' and 3' UTR sequences.

As used herein, the term "nucleic acid" refers to a polymer made up of nucleotide monomers. A nucleic acid can be single stranded or double stranded, and can be linear or circular. Where single-stranded, a nucleic acid can be a sense strand or an antisense strand. A nucleic acid can be composed of DNA (e.g., cDNA, genomic DNA, synthetic DNA, or a combination thereof), RNA, or DNA and RNA. Further, nucleic acids can contain information for gene expression, including, but not limited to, promoters, 5' UTRs, 3' UTRs, coding sequences, and terminators.

A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes one or more expression control sequences, and an "expression control sequence" is a DNA sequence that controls and regulates the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The terms "regulatory region," "control element," and "expression control sequence" refer to nucleotide sequences that influence transcription or translation initiation and rate, and stability and/or mobility of the transcript or polypeptide product. Regulatory regions include, without limitation, promoter sequences, enhancer sequences, response elements, protein recognition sites, inducible elements, promoter control elements, protein binding sequences, 5' and 3' UTRs, transcriptional start sites, termination sequences, polyadenylation sequences, introns, and other regulatory regions that can reside within coding sequences, such as secretory signals, Nuclear Localization Sequences (NLS) and protease cleavage sites.

As used herein, "operably linked" means incorporated into a genetic construct so that expression control sequences effectively control expression of a coding sequence of interest. A coding sequence is "operably linked" and "under the control" of expression control sequences in a cell when RNA polymerase is able to transcribe the coding sequence into RNA, which if an mRNA, then can be translated into the protein encoded by the coding sequence. Thus, a regulatory region can modulate, e.g., regulate, facilitate or drive, transcription in the plant cell, plant, or plant tissue in which it is desired to express a modified target nucleic acid.

A promoter is an expression control sequence composed of a region of a DNA molecule, typically within 100 nucleotides upstream of the point at which transcription starts (generally near the initiation site for RNA polymerase II). Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter. A promoter can, however, be positioned as much as about 5,000 nucleotides upstream of the translation start site, or about 2,000 nucleotides upstream of the transcription start site. A promoter typically comprises at least a core (basal) promoter. A promoter also may include at least one control element such as an upstream element. Such elements include upstream activation regions (UARs) and, optionally, other DNA sequences that affect transcription of a polynucleotide such as a synthetic upstream element.

The choice of promoters to be included depends upon several factors, including, but not limited to, efficiency, selectability, inducibility, desired expression level, and cell or tissue specificity. For example, tissue-, organ- and cell-specific promoters that confer transcription only or predominantly in a particular tissue, organ, and cell type, respectively, can be used. In some embodiments, promoters specific to vegetative tissues such as the stem, parenchyma, ground meristem, vascular bundle, cambium, phloem, cortex, shoot apical meristem, lateral shoot meristem, root apical meristem, lateral root meristem, leaf primordium, leaf mesophyll, or leaf epidermis can be suitable regulatory regions. In some embodiments, promoters that are essentially specific to seeds ("seed-preferential promoters") can be useful. Seed-specific promoters can promote transcription of an operably linked nucleic acid in endosperm and cotyledon tissue during seed development. Alternatively, constitutive promoters can promote transcription of an operably linked nucleic acid in most or all tissues of a plant, throughout plant development. Other classes of promoters include, but are not limited to, inducible promoters, such as promoters that confer transcription in response to external stimuli such as chemical agents, developmental stimuli, or environmental stimuli.

Non-limiting examples of promoters that can be included in the nucleic acid constructs provided herein include constitutively expressed promoters such as the cauliflower mosaic virus (CaMV) 35S transcription initiation region and maize ubiquitin-1 promoter, fruit-specific promoters such as the ACC-oxidase (Barry, *Plant J.* 9:525-535, 1996) and E8 promoters (Mehta, *Nat. Biotechnol.* 20:613-618, 2011), seed-specific promoters such as the HaG3-A (Bogue, *Mol. Gen. Genet.* 222:49-57, 1990) and Psl (de Pater, *Plant J.* 6:133-140, 1994) promoters, floral tissue-specific promoters such as the END1 (Gómez, *Planta* 219:967-981, 2004) and TomA108 (Xu, *Plant Cell Rep.* 25:231-240, 2006) promoters, root-specific promoters such as the B33 (Farran, *Transgenic Res.* 11:337-346, 2002) and RB7 (Vaughan, *J. Exp. Botany* 57:3901-3910, 2006) promoters, the 1' or 2' promoters derived from T-DNA of *Agrobacterium tumefaciens*, promoters from a maize leaf-specific gene described by Busk (*Plant J.* 11:1285-1295, 1997), kn1-related genes from maize and other species, and chemical-inducible promoters such as the XVE (Zuo et al., *The Plant Journal* 24:265-273, 2000) and GVG (Aoyama and Chua, *The Plant Journal* 11:605-612, 1997) promoter systems.

A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA message stability or translation attenuation. Examples of 3' UTRs include, without limitation, polyadenylation signals and transcription termination sequences. A polyadenylation region at the 3'-end of a coding region can also be operably linked to a coding sequence. The polyadenylation region can be derived from the natural gene, from various other plant genes, or from an *Agrobacterium* T-DNA.

The term "rare-cutting endonuclease" as used herein refers to a natural or engineered protein having endonuclease activity directed to a nucleic acid sequence with a recognition sequence (target sequence) about 12-40 bp in length (e.g., 14-40, 15-36, or 16-32 bp in length; see, e.g., Baker, *Nature Methods* 9:23-26, 2012). Typical rare-cutting endonucleases cause cleavage inside their recognition site, leaving 4 nt staggered cuts with 3'-OH or 5'-OH overhangs. In some embodiments, a rare-cutting endonuclease can be a meganuclease, such as a wild type or variant homing endonuclease (e.g., a homing endonuclease belonging to the dodecapeptide family (LAGLIDADG; SEQ ID NO:9) (see, WO 2004/067736). In some embodiments, a rare-cutting endonuclease can be a fusion protein that contains a DNA binding domain and a catalytic domain with cleavage activity. TALE-nucleases and zinc finger nucleases (ZFNs) are examples of fusions of DNA binding domains with the catalytic domain of the endonuclease FokI. Customized TALE-nucleases are commercially available under the trade name TALEN™ (Cellectis, Paris, France).

TALEs are found in plant pathogenic bacteria in the genus *Xanthomonas*. These proteins play important roles in disease, or trigger defense, by binding host DNA and activating effector-specific host genes (see, e.g., Gu et al., *Nature* 435:1122-1125, 2005; Yang et al., *Proc. Natl. Acad. Sci. USA* 103:10503-10508, 2006; Kay et al. *Science* 318:648-651, 2007; Sugio et al., *Proc. Natl. Acad. Sci. USA* 104: 10720-10725, 2007; and Römer et al. *Science* 318:645-648, 2007). Specificity depends on an effector-variable number of imperfect, typically 34 amino acid repeats (Schornack et al., *J. Plant Physiol.* 163:256-272, 2006; and WO 2011/072246). Polymorphisms are present primarily at repeat positions 12 and 13, which are referred to herein as the repeat variable-diresidue (RVD).

The RVDs of TALEs correspond to the nucleotides in their target sites in a direct, linear fashion, one RVD to one nucleotide, with some degeneracy and no apparent context dependence. This mechanism for protein-DNA recognition enables target site prediction for new target specific TALEs, as well as target site selection and engineering of new TALEs with binding specificity for the selected sites.

TALE DNA binding domains can be fused to other sequences, such as endonuclease sequences, resulting in chimeric endonucleases targeted to specific, selected DNA sequences, and leading to subsequent cutting of the DNA at or near the targeted sequences. Such cuts (double-stranded breaks) in DNA can induce mutations into the wild-type DNA sequence via NHEJ or homologous recombination, for example. In some cases, TALE-nucleases can be used to facilitate site directed mutagenesis in complex genomes, knocking out or otherwise altering gene function with great precision and high efficiency. As described in the Examples below, TALE-nucleases targeted to the *Nicotiana benthamiana* ALS gene can be used to mutagenize the endogenous gene, confirmed by indels at the target site. The fact that some endonucleases (e.g., FokI) function as dimers can be used to enhance the target specificity of the TALE-nuclease. For example, in some cases a pair of TALE-nuclease monomers targeted to different DNA sequences (e.g., the underlined target sequences shown in FIG. 1; SEQ ID NOS:2 and 3) can be used. When the two TALE-nuclease recognition sites are in close proximity, as depicted in FIG. 1, the inactive monomers can come together to create a functional enzyme that cleaves the DNA. By requiring DNA binding to activate the nuclease, a highly site-specific restriction enzyme can be created.

In some embodiments, the methods provided herein can include the use of programmable RNA-guided endonucleases, or portions (e.g., subunits) thereof. RNA-guided endonucleases are a new genome engineering tool that has been developed based on the RNA-guided CRISPR (Clustered Regularly Interspaced Short Palindromic Repeats)-associated nuclease (Cas9) from the type II prokaryotic CRISPR adaptive immune system (see, e.g., Belahj et al., *Plant Methods* 9:39, 2013). This system can cleave DNA sequences that are flanked by a short sequence motif known as a proto-spacer adjacent motif (PAM). Cleavage is achieved by engineering a specific CRISPR RNA (crRNA) that is complementary to the target sequence that associates with the Cas9 endonuclease. In this complex, the trans-activating crRNA (tracrRNA):crRNA complex acts as a guide RNA that directs the Cas9 endonuclease to the cognate target sequence. A synthetic single guide RNA (sgRNA) also has been developed that, on its own, is capable of targeting the Cas9 endonuclease. This tool can be expressed utilizing the UTR sequences described herein, to genetically engineer plant cells. Thus, in some embodiments, the coding sequence of the Cas9 endonuclease and sgRNA or tracrRNA:crRNA can be transiently expressed from the expression plasmids as provided herein.

Another programmable RNA-guided endonuclease of a class 2 CRISPR-Cas system also has been described and used for gene editing purposes (Zetsche et al., *Cell* 163:759-771, 2015). This system uses a non-specific endonuclease unit from the Cpf1 protein family, with a specificity of cleavage conferred by a single crRNA (lacking tracr RNA). Similar to Cas9, the Cpf1 coding sequence can be fused to UTR sequences described herein to improve its stability, and thus the efficiency of the resulting gene editing method.

Accordingly, this document also provides a method for gene editing using a programmable RNA-guide endonuclease system, where the Cas9 or Cpf1 coding sequence is fused to a suitable stabilizing UTR sequence, such as those disclosed herein.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, a nucleic acid sequence that has 240 matches when aligned with the sequence set forth in SEQ ID NO:1 is 94.9 percent identical to the sequence set forth in SEQ ID NO:3 (i.e., 240÷253×100=94.9). It is noted that the percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. It also is noted that the length value will always be an integer.

This document provides expression plasmids that contain (a) a coding sequence and (b) a 5' UTR, a 3' UTR, or both a 5' UTR and a 3' UTR. In some embodiments, the 5' UTR can have the sequence set forth in SEQ ID NO:10 or SEQ ID NO:12, or a sequence with at least 95 percent identity to SEQ ID NO:10 or SEQ ID NO:12. In some embodiments, the 3' UTR can have the sequence set forth in SEQ ID NO:11 or SEQ ID NO:13, or a sequence with at least 95 percent identity to SEQ ID NO:11 or SEQ ID NO:13. In some embodiments, the 5' UTR can have the sequence set forth in SEQ ID NO:10, or a sequence with at least 95 percent identity to SEQ ID NO:10, and the 3' UTR can have the sequence set forth in SEQ ID NO:11, or a sequence with at least 95 percent identity to SEQ ID NO:11. In some embodiments, the 5' UTR can have the sequence set forth in SEQ ID NO:12, or a sequence with at least 95 percent identity to SEQ ID NO:12, and the 3' UTR can have the sequence set forth in SEQ ID NO:13, or a sequence with at least 95 percent identity to SEQ ID NO:13. The expression plasmids provided herein can be constructed for in vitro expression of mRNA transcripts or for expression in planta.

An expression plasmid as provided herein can contain, for example, (a) a 5' promoter region, (b) a 5' UTR, (c) a structural coding sequence encoding a polypeptide, and (d) a polyadenylated tail [poly(A)-tail], where the 5' promoter region and the 5' UTR are operably linked to the structural coding sequence, such that the polypeptide encoding sequence can be transiently expressed in a plant cell after introduction of the plasmid into the plant cell. In some embodiments, an expression plasmid as provided herein can contain (a) a 5' promoter region, (b) a structural coding sequence encoding a polypeptide, (c) a 3' UTR, and (d) a poly(A)-tail, where the 5' promoter region and the 3' UTR are operably linked to the structural coding sequence, such that the polypeptide encoding sequence can be transiently expressed in a plant cell after introduction of the plasmid into the plant cell. In some embodiments, an expression plasmid can contain (a) a 5' promoter region, (b) a 5' UTR, (c) a structural coding sequence encoding a polypeptide, (d) a 3' UTR, and (e) a poly(A)-tail, where the 5' promoter region, 5' UTR, and 3' UTR are operably linked to the structural coding sequence, such that the polypeptide encoding sequence can be transiently expressed in a plant cell after introduction of the plasmid into the plant cell.

The 5' promoter region can exist naturally in a plant cell, or can be capable of naturally entering a plant cell (e.g., a promoter sequence that may have originated in either a bacterial system such as *Agrobacterium*, or a viral system such as Geminivirus). The 5' promoter region can include a constitutive promoter or an inducible promoter. When the promoter is inducible, the methods provided herein can include inducing the promoter.

The polypeptide-encoding sequence can encode a rare-cutting endonuclease or rare-cutting endonuclease subunit (e.g., a monomer of an endonuclease that functions as a dimer). The rare-cutting endonuclease can be, for example, a transcription activator-like (TAL) effector endonuclease, a ZFN, a meganuclease, or a programmable RNA-guided endonuclease. Transient expression of the rare-cutting endonuclease can result in site-directed mutagenesis.

Any suitable UTR or combination of UTRs can be used. As described in the Examples herein, for example, certain UTRs derived from *Arabidopsis thaliana* mRNA transcripts are capable of increasing the stability of mRNA-encoding sequence-specific nucleases when operably linked to the polypeptide-encoding sequence. Such UTRs can be from the gene At1G09740 (SEQ ID NOS:10 and 11), which is annotated as being involved in cellular response to iron ion starvation, iron ion transport, nitrate transport, response to molecules of fungal origin, and response to nitrate. This protein codes for a universal stress protein A (UspA) domain, which is a small cytoplasmic bacterial protein whose expression is enhanced when the cell is exposed to stress agents (The *Arabidopsis* Information Resource [TAIR], available online at arabidopsis.org/servlets/TairObject?type=locus&name=At1g09740). The At1G09740 mRNA transcript was determined to have a half-life of 73.8 hours in a genome-wide analysis of mRNA decay rates in *A. thaliana* (Narsai et al., *Plant Cell* 19:3418-3436, 2007). Thus, in some embodiments, increased stability granted by the At1G09740 UTRs can allow site-specific nucleases to be expressed at a higher and more sustained level, resulting in increased frequency of targeted mutagenesis.

In some cases, UTRs derived from *A. thaliana* mRNA transcripts can decrease the stability of mRNA encoding sequence-specific nucleases. Such UTRS can be from the gene At5G28050 (SEQ ID NOS:12 and 13), which is annotated as being involved purine nucleoside catabolic process, and functions in zinc ion binding (The *Arabidopsis* Information Resource [TAIR], supra). The At5G28050 mRNA transcript was determined to have a half-life of 34.1 hours in a genome-wide analysis of mRNA decay rates in *A. thaliana* (Narsai et al., supra). Thus, in some cases, decreased stability granted by the At5G28050 UTRs can allow site-specific nucleases to be expressed at a lower level, which can be useful in applications that benefit from reduced transcription (e.g., reduced toxicity, reduced off-target cleavage, reduction of gene copies targeted).

Other examples of UTR sequences that may be useful in the materials and methods provided herein are described by Narsai et al. (supra), which contains a list of several thousand genes with UTRs that could have effects similar to those of the At1G09740 gene.

This document also provides host cells containing expression plasmids as described herein. Suitable host cells include, without limitation, plant cells or plant cell lines (e.g., protoplasts, mesophyll cells, hypocotyl cells, or undifferentiated calli cells), bacterial cells, yeast cells, and animal cells (e.g., non-human cells, or cells derived from an animal such as a mammal).

In addition, this document provides methods for modulating (e.g., increasing or decreasing) the transient expression of a polypeptide in a plant cell. The methods can include, for example, introducing into a plant cell a nucleic acid that includes (a) a 5' promoter region, (b) an optional 5' UTR, (c) a structural coding sequence encoding a polypeptide, (d) an optional 3' UTR, and (e) a poly(A)-tail, where one or both of the 5' UTR and the 3' UTR are present, where the 5' promoter region, 5' UTR (when present), and 3' UTR (when present) are operably linked to the structural coding sequence such that the polypeptide is transiently expressed in the plant cell. As described above, the 5' promoter region can exist naturally in a plant cell or can be capable of naturally entering a plant cell, the 5' promoter region can include a constitutive promoter or an inducible promoter (in which case the methods can include inducing the promoter), and the polypeptide-encoding sequence can encode a rare-cutting endonuclease or rare-cutting endonuclease subunit targeted to a DNA sequence (e.g., an endogenous genomic sequence) within the plant cell. Transient expression of the rare-cutting endonuclease in the plant cell can result in site-directed mutagenesis when the endonuclease cleaves the DNA at its target site.

Any suitable method can be used to introduce the nucleic acid into the plant cell. In some embodiments, for example, a method as provided herein can include contacting a plant cell with an organism that is capable of horizontal gene transfer (e.g., a bacterium, such as an *Agrobacterium*), where the organism contains a Ti or Ri plasmid having a T-DNA region that includes the promoter, UTRs, coding sequence, and poly-A tail. In other embodiments, a method for modulating the transient expression of a polypeptide in a plant cell can include using PEG-mediated, biolistics-mediated, or electroporation-mediated transformation of a plant cell (e.g., a protoplast) to introduce a plasmid containing the nucleic acid.

This document also provides methods for generating plants. The methods can include, for example, (a) introducing into a plant cell a nucleic acid that includes (i) a 5' promoter region, (ii) an optional 5' UTR, (iii) a polypeptide-encoding sequence, (iv) an optional 3' UTR, and (v) a poly(A)-tail, where one or both of the 5' UTR and the 3' UTR are present, and where the 5' promoter region, 5' UTR (when present), and 3' UTR (when present) are operably linked to the structural coding sequence such that the polypeptide is transiently expressed in the plant cell, and (b) regenerating the plant cell into a plant. The polypeptide-encoding sequence can encode a rare-cutting endonuclease or a rare-cutting endonuclease subunit, and the regenerated plant can contain one or more mutations generated by transient expression of the rare-cutting endonuclease.

Again, any suitable method can be used to introduce the plasmid into the plant cell. For example, the plant cell can be contacted with an organism capable of horizontal gene transfer (e.g., an *Agrobacterium*) that contains a modified Ti or Ri plasmid having a T-DNA region that includes the above-referenced nucleic acid, such that the polypeptide-encoding sequence is expressed in the plant cell. In other embodiments, PEG-mediated, biolistics-mediated, or electroporation-mediated transformation can be used to introduce an expression plasmid containing the above-referenced nucleic acid into the plant cell.

In some embodiments, methods for using rare-cutting endonucleases (e.g., TALE-nucleases or CRISPR/Cas-based nucleases) operably linked to a 5' UTR, a 3' UTR, or a 5' UTR and a 3' UTR to generate plants, plant cells, or plant parts having mutations in endogenous genes can include, for example, using vectors as described in the Examples herein. For example, one or more nucleic acids encoding TALE-nucleases targeted to selected sequences (e.g., the ALS2 sequence shown in FIG. 1) can be transformed into plant cells (e.g., protoplasts, mesophyll cells, hypocotyl cells, or undifferentiated calli cells), where they can be expressed. In some cases, one or more TALE-nuclease proteins can be introduced into plant cells (e.g., protoplasts). The plant cells, or a plant cell line or plant part(s) generated from the plant cells, can subsequently be analyzed to determine whether mutations have been introduced at the target site(s), using nucleic acid-based assays (e.g., PCR and DNA sequencing, or PCR followed by a T7E1 assay; Mussolino et al., *Nucleic Acids Res.* 39:9283-9293, 2011) to detect mutations at the genomic loci.

This document also provides articles of manufacture that include one or more expression plasmids as described herein, in combination with packaging material and one or more additional components (e.g., buffers or other reagents) for use in the methods described herein. In some embodiments, an article of manufacture can include host cells transformed with an expression plasmid as provided herein. The one or more plasmids and/or the host cells can be packaged using packaging material well known in the art to prepare an article of manufacture. An article of manufacture also can have a label (e.g., a tag or label secured to the packaging material, a label printed on the packaging material, or a label inserted within the package). The label can indicate that the plasmid(s) and/or host cells contained within the package can be used to generate genetically modified plants, for example.

The invention will be further described in the following examples, which do not limit the scope of the invention described in the claims.

EXAMPLES

Example 1—Engineering Sequence-Specific Nucleases to Mutagenize the ALS2 Gene

To completely inactivate or knock-out the ALS2 gene in *N. benthamiana*, software that specifically identifies TALE nuclease recognition sites (e.g., TALE-NT 2.0; Doyle et al., *Nucleic Acids Res* 40:W117-122, 2012) was used to design sequence-specific nucleases targeted to sequences just downstream of the ALS2 protein coding sequence. The TALE-nuclease target sites for the ALS2 gene are shown in FIG. 1 and also in TABLE 1 below; this TALE-nuclease pair is designated ALS2_T1. TALE-nucleases were obtained from Cellectis Bioresearch (Paris, France).

Example 2—ALS2-T1 TALE Nuclease Activity in Yeast

To assess the activity of the TALE-nucleases targeting the ALS2 gene, activity assays were performed in yeast using methods similar to those described elsewhere (Christian et al., *Genetics* 186:757-761, 2010). For these assays, a target plasmid was constructed with the TALE-nuclease recognition sites cloned into a non-functional β-galactosidase reporter gene; the plasmid was transformed into yeast using PEG-mediated transformation (Sigma; St. Louis, Mo.). The sequence containing the target sites was flanked by a direct repeat of β-galactosidase coding sequence, so that if the reporter gene was cleaved by the TALE-nuclease pair (expressed from the translational elongation factor EF-1 alpha (TEF1) promoter), recombination would occur between the direct repeats and function would be restored to the β-galactosidase gene. β-galactosidase activity therefore served as a measure of TALE-nuclease cleavage activity. In the yeast assay, the ALS2_T1 TALE-nuclease pair displayed cleavage activity. Activities were normalized to the benchmark nuclease, I-SceI. Results are summarized in TABLE 2.

Example 3—Construction of Enhanced Stability Expression Plasmids

Figure 3:
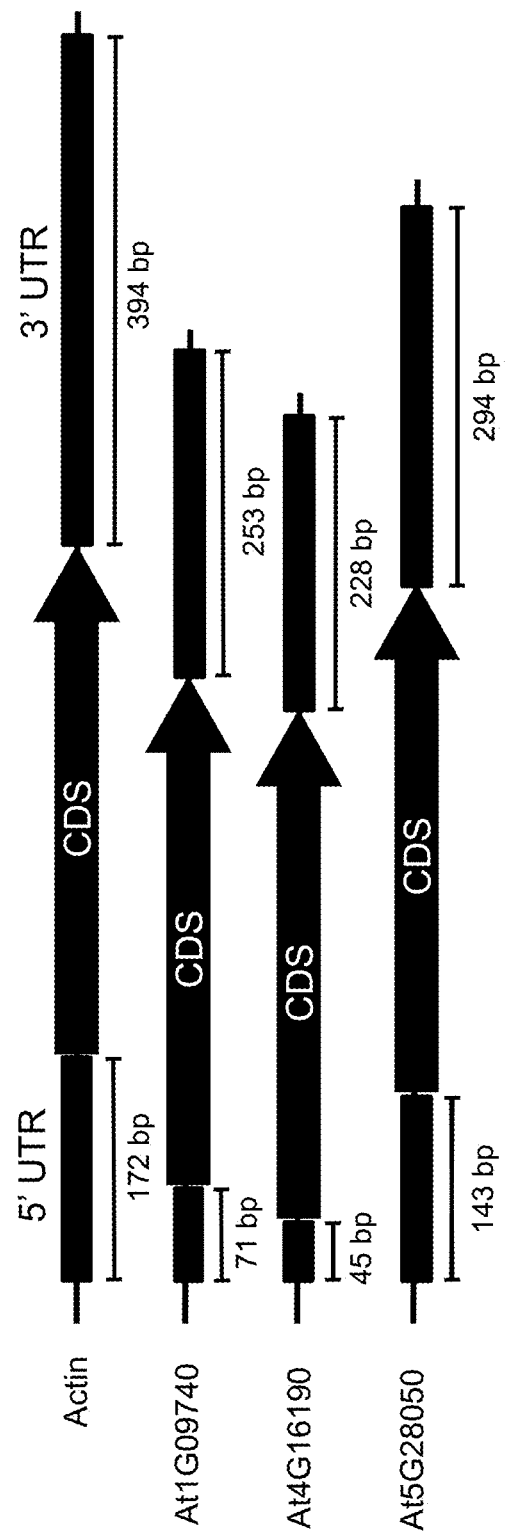
FIG. 3 is an illustration depicting the transcribed sequences containing the four UTR pairs tested.
Figure 4:
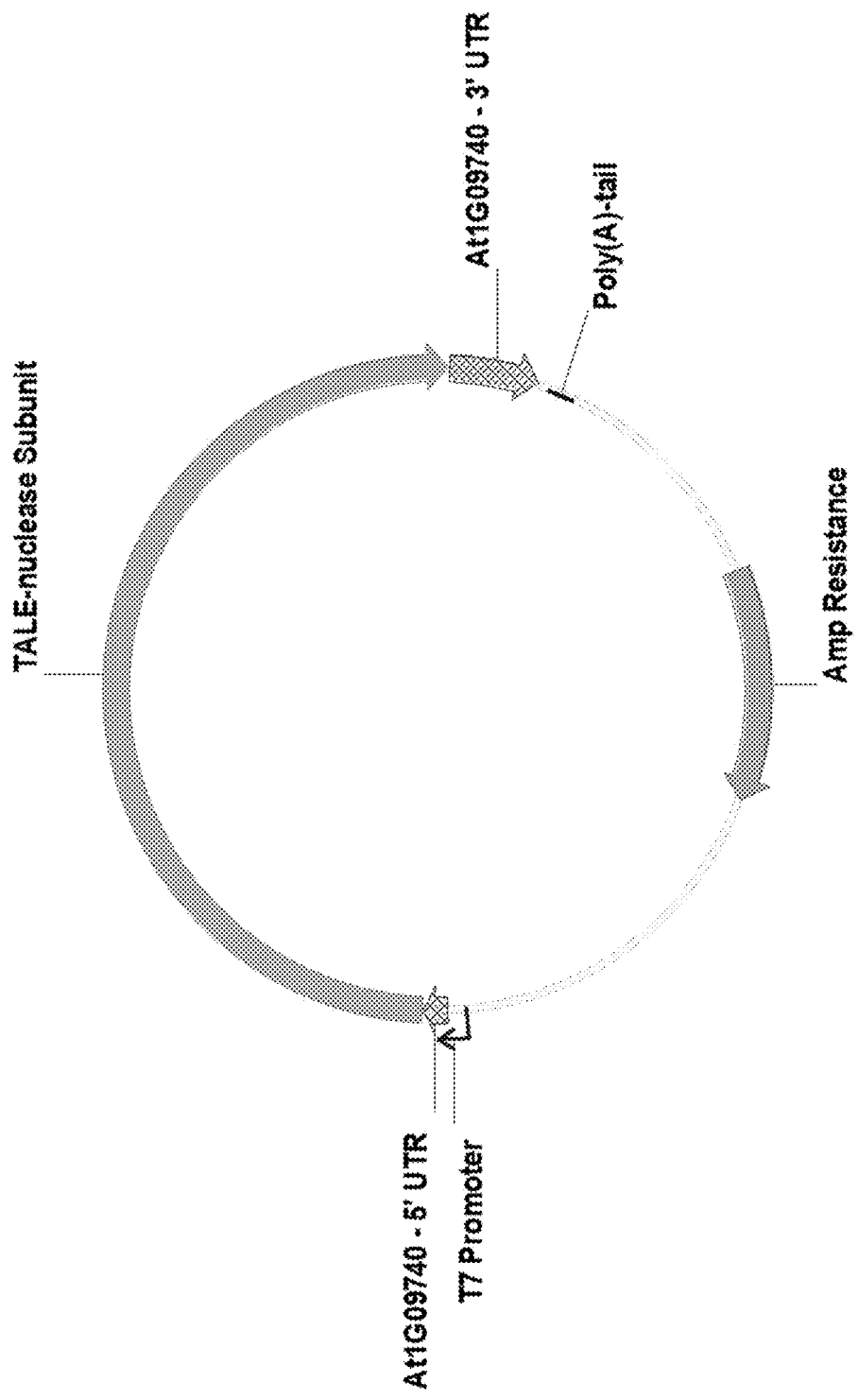
FIG. 4 is a diagram of a modified pSP72 vector comprising the At1G09740 5' UTR, a sequence encoding a TALE-nuclease subunit, and the At1G09740 3' UTR.

To achieve transient expression of desired nucleases without integration of exogenous DNA into the genome of a targeted cell, an mRNA expression vector was synthesized that included the 5' and 3' UTRs from either At1G09740 (SEQ ID NOS:10 and 11), At5G28050 (SEQ ID NOS:12 and 13), actin (SEQ ID NOS:14 and 15), or At4G16190 (SEQ ID NOS:16 and 17) (FIG. 3). The effects of adding these UTRs to the expression constructs was assessed to determine the level of increased stability and/or translational efficiency for the nuclease or nuclease mRNA, as measured by NHEJ frequencies. To construct the enhanced mRNA expression plasmid, the pSP72 plasmid (Promega; Madison, Wis.) (FIG. 2) was modified using restriction enzymes to insert a synthesized cassette (Integrated DNA Technologies; Coralville, Iowa) containing: (i) 5' UTR sequence, (ii) linker sequence, and (iii) 3' UTR sequence. This cassette was synthesized and ligated into the modified pSP72 utilizing sticky end restriction site ligation. After verification in *E. coli*, this plasmid was subjected to restriction enzyme digests followed by ligation of the TALE-nuclease subunits to yield the desired product (FIG. 4).

Example 4—Increased NHEJ Frequency in *N. benthamiana* Protoplasts Using Expression Vectors Containing 5' and 3' UTRs TALE-nuclease activity at endogenous target sites in *N. benthamiana* was measured by expressing the TALE-nucleases operably linked to the 5' and 3' UTRs from either At1G09740 (SEQ ID NOS:10 and 11), At5G28050 (SEQ ID NOS:12 and 13), actin (SEQ ID NOS:14 and 15), or At4G16190 (SEQ ID NOS:16 and 17) in protoplasts and subsequently surveying the target sites for mutations introduced by NHEJ. Methods for protoplast preparation were performed as described elsewhere (Wright et al., *Plant J.* 44:693-705, 2005). Briefly, seeds were sterilized by washing them successively with 100% ethanol, 50% bleach and then sterile distilled water. The sterilized seeds were planted on MS agarose medium supplemented with iron. Protoplasts were isolated from young expanded leaves using the protocol described by Wright et al. (supra).

Plasmids containing TALE nuclease coding sequences operably linked to the 5' and 3' UTRs, together a plasmid encoding yellow fluorescent protein (YFP), were introduced into *N. benthamiana* protoplasts by polyethylene glycol- (PEG-) mediated transformation (Yoo et al., *Nature Protocols* 2:1565-1572, 2007). Twenty-four hours after treatment, transformation efficiency was measured using a fluorescent microscope to monitor YFP fluorescence in an aliquot of the transformed protoplasts. The remainder of the transformed protoplasts were harvested, and genomic DNA was prepared using a hexadecyltrimethylammonium bromide- (CTAB-) based method. Using genomic DNA prepared from the protoplasts as a template, a 235-bp fragment encompassing the TALE-nuclease recognition site was amplified by PCR. Sequencing reads with insertion/deletion (indel) mutations in the spacer region were considered to be derived from imprecise repair of a cleaved TALE-nuclease recognition site by NHEJ. Mutagenesis frequency was calculated as the number of sequencing reads with NHEJ mutations out of the total sequencing reads.

Figure 7:
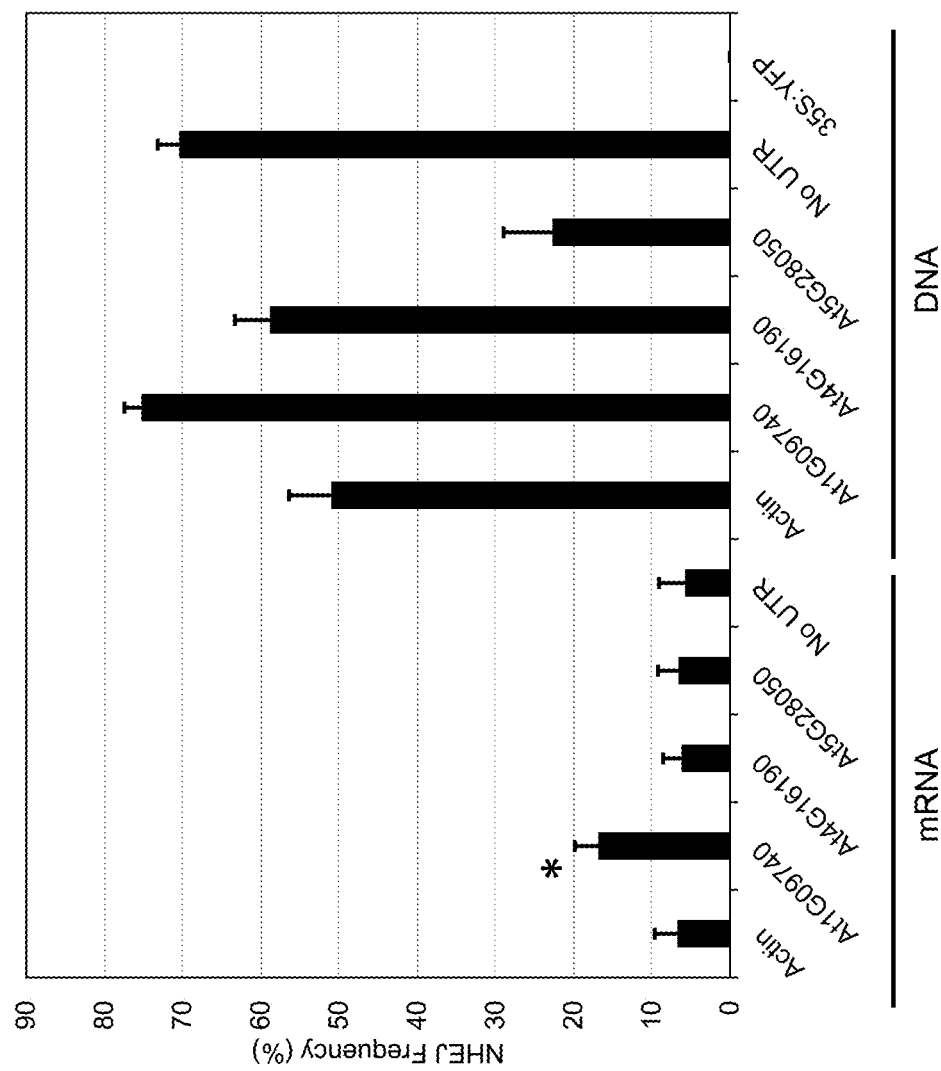
FIG. 7 is a graph plotting NHEJ mutation frequencies for the TALE-nuclease when the coding sequence was fused to different UTR pairs. TALE-nuclease and UTR sequences were delivered to cells as either mRNA or DNA, as indicated.

Three biological replicates were performed. The activities of the ALS2 TALE-nuclease pairs, with or without the addition of UTRs, are summarized in TABLE 3. When the TALE-nucleases were delivered as mRNA with the At1G09740 UTRs, a NHEJ frequency of 15.5% was observed at the ALS2 loci, as compared to 5.1% for mRNA encoding TALE-nucleases delivered with the At5G28050 UTRs, and 7.7% for transformations in which the TALE-nuclease-encoding mRNA did not contain the UTRs. When the TALE-nucleases were delivered as DNA with the At1G09740 UTRs, a NHEJ frequency of 77.3% was observed at the ALS2 loci, as compared to 27.1% for transformation in which the TALE-nuclease-encoding DNA was delivered with the At5G28050 UTRs, and 70.7% for transformations in which the TALE-nuclease-encoding DNA did not contain the UTRs. Examples of TALE-nuclease-induced mutations at ALS2 are shown in FIGS. 5 and 6. A summary of mutation frequencies from all four UTR pairs is shown in FIG. 7.

Figure 8:
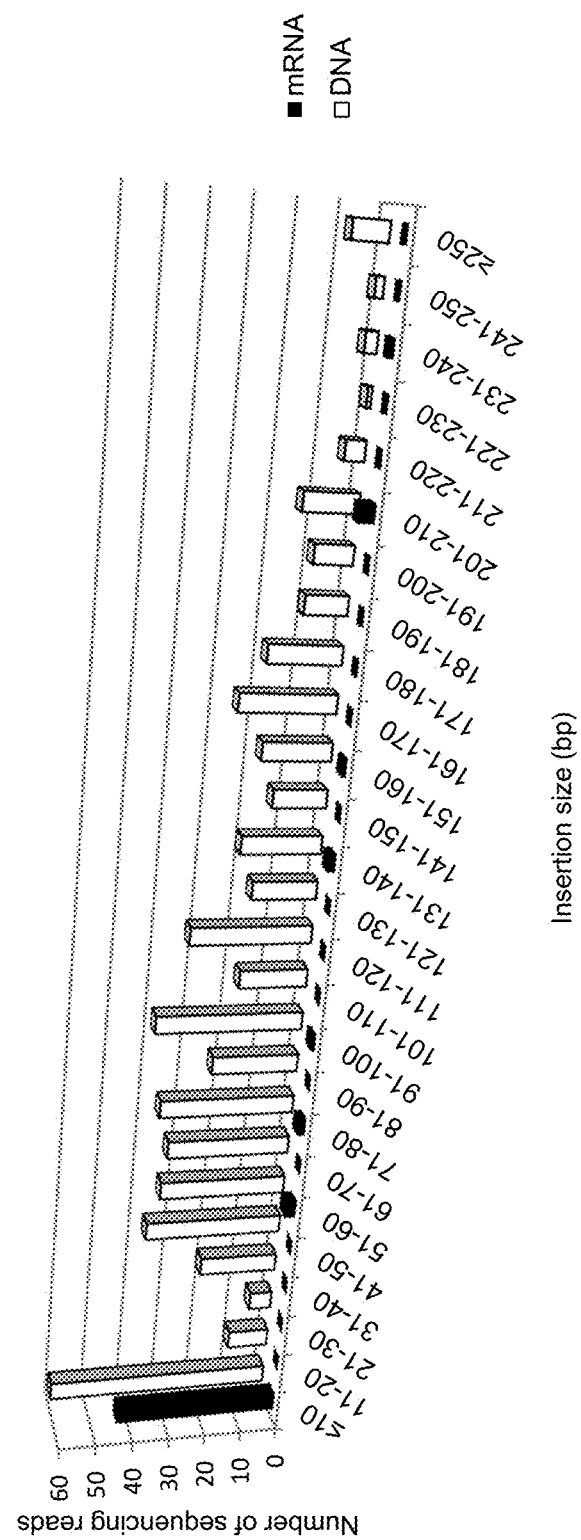
FIG. 8 is a graph plotting the number of insertions within the TALE-nuclease target site vs. the size of the insertion.

Example 5—Decreased Insertion Frequencies when TALE-Nucleases are Delivered by mRNA A benefit of using mRNA over DNA for nuclease delivery is that plants without foreign DNA are more likely to be created, and this may lessen the regulatory burden for crop varieties created through genome engineering. Consistent with this hypothesis, the analysis of the insertion/deletion (indel) mutation profile from the 454 pyrosequencing data revealed a large disparity in the types of mutations created by mRNA and DNA reagents. Cells transformed with DNA constructs had an average insertion frequency of 6.25%, compared to a 1.98% insertion frequency for cells transformed with mRNA. Among the insertions created with DNA reagents, 88% were >10 bp, with a median insertion size of 90 bp (FIG. 8). In contrast, only 24% of insertions resulting from mRNA delivery were >10 bp, with a median insertion size of a 3 bp. For the DNA transformation experiments, the majority (>90%) of insertions ≥10 bp were derived from the plasmid vector; that is, the inserted sequence originated from the TALEN-encoding plasmid. In contrast, only one of the insertions resulting from the mRNA transformation experiments had an insertion (131 bp) that matched the TALEN coding sequence. This insertion may have arisen from DNA contamination if the expression vector was not completely digested by DNase treatment after in vitro transcription.

Taken together, these data indicate that mRNA delivery yields mutation profiles that only rarely involve DNA insertion, which may be an advantage for creating plants that contain mutations but to not contain foreign DNA.

At1G09740 5' UTR Sequence
(SEQ ID NO: 10)
ctcttgaactttccaagagttgaagaaaatcacagaaagccttagcacag
agaagagagattgaagaagtc At1G09740 3' UTR Sequence
(SEQ ID NO: 11)
agaggatatatatgtacatatgcaaagggatatcaagaccatctgtaatc ttttgaagttttgtgaagctatagaagccaagcaagaattctaccagatt acttcccaaataagtggtgtgaatgtaaattaataagagctacagaaaca ttgattggctcagtgtatgtgttgtattcatattcgttgttttattttat acggttgagaattgaataatgttgttgcatcaaatcactatgaaggacat ttacag At5G28050 5' UTR Sequence
(SEQ ID NO: 12)
ctcaattttggactcgtctgcttttgtttatataaacacttctcttcttc
ttcaatctccacacacaccacacaaaaccacctaccttcttcgatttctc
cagaaatcctccttcaagttcatactcatggaagaagctaaag At5G28050 3' UTR Sequence
(SEQ ID NO: 13)
agcacttctccattaccacattcttcttcttcttctccttcatgatggta attagaagtagtagaagaagaactgcacttgctttaacttaaataaatct ctgtttcaaattgttcattttaaaaacagaaggaaacgaaaaaaaaaatc aatttcggttcttgttgacacgatttgtaatttcttttcttcatttgaat tgaactggtaaatactttcttctctgtcaaaatctttattttctattttc tgtacaaggccaagttcttcactaataaatcgaattgtttttcta Actin 5' UTR Sequence
(SEQ ID NO: 14)
agaaaaaaataaaagagtgagaaaaatcgtagagctatatattcgcacat gtactcgtttcgctttccttagtgttagctgctgccgctgttgtttctcc tccatttctctatctttctctctcgctgcttctcgaatcttctgtatcat cttcttcttcttcaagtgaaaa Actin 3' UTR Sequence
(SEQ ID NO: 15)
gtgtgtcttgtcttatctggttcgtggtggtgagtttgttacaaaaaaat ctattttccctagttgagatgggaattgaactatctgttgttatgtggat tttattttcttttttctctcttttagaaccttatggttgtgtcaagaagtctt gtgtactttagttttatatctctgttttatctcttctatttttctttagga tgcttgtgatgatgctgttttttttttgtccctaagcaaaaaaatatcata ttatatttggtccttggttcattttttttggtttttttttgtcttcacata taaatattgtttgaatgtcttcaatcttttatttgtatgagacaattatt taagtatcgggtgacaatgcagctattatgtattgtcgattgtt At4G16190 5' UTR Sequence
(SEQ ID NO: 16)
tgtccccaaagtctcctcttccttatctcttggaaaccaagaagc At4G16190 3' UTR Sequence
(SEQ ID NO: 17)
aattattaggacactacctgtctatctttgtgtatatgtatgtatggttg cataaagatactacgaacttttatcgttagtattgtgtctctgtttcagc ttttaatgtaaaatagcttgggggtattatctttgtagcattgaatgctt aagatgataatatgatatgattatcaaattattataagttggaacttgga ataatagaaattttatatgttttatatt

TABLE 1

ALS2_T1 TALE-nuclease target sequences

| Target Sequence Left | SEQ ID: | Target Sequence Right | SEQ ID: |
|---|---|---|---|
| TAGCTTGTTCCACATTT | 2 | TGTCATGCTGGGTCAG | 3 |

TABLE 2

ALS2 TALE-nuclease activity in yeast

| | Activity in yeast* | |
|---|---|---|
| Target Subunit | ALS2_T1 37° C. | ALS2_T1 30° C. |
| ALS2 T01 Left ALS2 T01 Right | 0.97 (0.02) | 0.86 (0.02) |

*Normalized to I-SceI (max = 1.0)

TABLE 3

454 Sequencing Data

| Construct | UTR SEQ ID NOS: | Nucleic Acid Delivered | Mean NHEJ Frequency (%) | Standard Error |
|---|---|---|---|---|
| ALS2 TALE nuclease with UTR | 10 and 11 | mRNA | 15.53 | 2.97 |
| ALS2 TALE nuclease with UTR | 12 and 13 | mRNA | 5.13 | 2.58 |
| ALS2 TALE nuclease no UTR | N/A | mRNA | 7.69 | 3.32 |
| ALS2 TALE nuclease with UTR | 10 and 11 | DNA | 77.31 | 2.15 |
| ALS2 TALE nuclease with UTR | 12 and 13 | DNA | 27.09 | 6.23 |
| ALS2 TALE nuclease no UTR | N/A | DNA | 70.68 | 2.73 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for modifying the genomic material of a plant, plant part, or plant cell, comprising directly introducing into the plant, plant part, or plant cell a messenger RNA (mRNA) comprising (a) a structural coding sequence encoding a rare-cutting endonuclease or a rare-cutting endonuclease subunit targeted to a genomic sequence within the plant cell, wherein the rare-cutting endonuclease is a transcription activator-like effector-endonuclease, a meganuclease, or a programmable RNA-guided endonuclease, and (b) an RNA-stabilizing 5' untranslated region (UTR), is operably linked to the structural coding sequence, and wherein the 5' UTR comprises the nucleic acid sequence set forth in SEQ ID NO:10, with the proviso that the T's in SEQ ID NO:10 are U's.

2. The method of claim 1, wherein the plant, plant part, or plant cell is a dicotyledonous or monocotyledonous plant, plant part, or plant cell.

3. The method of claim 1, further comprising regenerating the plant cell or plant part into a plant.

4. A method for modifying the genomic material of a plant, plant part, or plant cell, comprising directly introducing into the plant, plant part, or plant cell an mRNA comprising (a) a structural coding sequence encoding a rare-cutting endonuclease or a rare-cutting endonuclease subunit targeted to a genomic sequence within the plant cell, wherein the rare-cutting endonuclease is a transcription activator-like effector-endonuclease, a meganuclease, or a programmable RNA-guided endonuclease, and (b) an RNA-stabilizing 3' UTR, wherein the 3' UTR is operably linked to the structural coding sequence, and wherein the 3' UTR comprises the nucleic acid sequence set forth in SEQ ID NO:11, with the proviso that the T's in SEQ ID NO:11 are U's.

5. The method of claim 4, wherein the plant, plant part, or plant cell is a dicotyledonous or monocotyledonous plant, plant part, or plant cell.

6. The method of claim 4, further comprising regenerating the plant cell or plant part into a plant.

7. A method for modifying the genomic material of a plant, plant part, or plant cell, comprising directly introducing into the plant, plant part, or plant cell a messenger RNA (mRNA) comprising (a) a structural coding sequence encoding a rare-cutting endonuclease or a rare-cutting endonuclease subunit targeted to a genomic sequence within the plant cell, wherein the rare-cutting endonuclease is a transcription activator-like effector-endonuclease, a meganuclease, or a programmable RNA-guided endonuclease, and (b) RNA-stabilizing 5' and 3' UTRs, wherein the 5' UTR and the 3' UTR are operably linked to the structural coding sequence, wherein the 5' UTR comprises the nucleic acid sequence set forth in SEQ ID NO:10, and wherein the 3' UTR comprises the nucleic acid sequence set forth in SEQ ID NO:11, with the proviso that the T's in SEQ ID NO:10 and SEQ ID NO:11 are U's.

8. The method of claim 7, wherein the plant, plant part, or plant cell is a dicotyledonous or monocotyledonous plant, plant part, or plant cell.

9. The method of claim 7, further comprising regenerating the plant cell or plant part into a plant.

* * * * *

SEQUENCE LISTING

<160> NUMBER OF SEQ ID NOS: 23

<210> SEQ ID NO 1
<211> LENGTH: 253
<212> TYPE: DNA
<213> ORGANISM: Nicotiana benthamiana

<400> SEQUENCE: 1

```
gctttgctca tcgtcactgt tgtactatta agtagttgat atttatgttt gttttgcatc      60
atcccctttt ggttttgaat gtgaaggatt tcagcaaagt ttcatcctct atttgcaaca     120
atctggagat taatttctaa tggagtagtt tagtgtaata agttagctt gttccacatt      180 tttatttcat aagctatgtc atgctgggtc agattggaac ttcctcttta ggttggatgt     240
aatccctatt agg                                                         253
```

<210> SEQ ID NO 2
<211> LENGTH: 17
<212> TYPE: DNA
<213> ORGANISM: Nicotiana benthamiana

```
<400> SEQUENCE: 2
tagcttgttc cacattt                                                     17

<210> SEQ ID NO 3
<211> LENGTH: 16
<212> TYPE: DNA
<213> ORGANISM: Nicotiana benthamiana

<400> SEQUENCE: 3
tgtcatgctg ggtcag                                                      16

<210> SEQ ID NO 4
<211> LENGTH: 48
<212> TYPE: DNA
<213> ORGANISM: Nicotiana benthamiana

<400> SEQUENCE: 4
tagcttgttc cacatttta tttcataagc tatgtcatgc tgggtcag                    48

<210> SEQ ID NO 5
<211> LENGTH: 41
<212> TYPE: DNA
<213> ORGANISM: Artificial Sequence
<220> FEATURE:
<223> OTHER INFORMATION: mutated sequence

<400> SEQUENCE: 5
tagcttgttc cacatttta agctatgtca tgctgggtca g                           41

<210> SEQ ID NO 6
<211> LENGTH: 34
<212> TYPE: DNA
<213> ORGANISM: Artificial Sequence
<220> FEATURE:
<223> OTHER INFORMATION: mutated sequence

<400> SEQUENCE: 6
tagcttgttc cacattttg tcatgctggg tcag                                   34

<210> SEQ ID NO 7
<211> LENGTH: 41
<212> TYPE: DNA
<213> ORGANISM: Artificial Sequence
<220> FEATURE:
<223> OTHER INFORMATION: mutated sequence

<400> SEQUENCE: 7
tagcttgttc cacatttta tgctatgtca tgctgggtca g                           41

<210> SEQ ID NO 8
<211> LENGTH: 44
<212> TYPE: DNA
<213> ORGANISM: Artificial Sequence
<220> FEATURE:
<223> OTHER INFORMATION: mutated sequence

<400> SEQUENCE: 8
tagcttgttc cacatttta tttagctatg tcatgctggg tcag                        44

<210> SEQ ID NO 9
<211> LENGTH: 9
<212> TYPE: PRT
<213> ORGANISM: Artificial Sequence
<220> FEATURE:
<223> OTHER INFORMATION: consensus
```

<400> SEQUENCE: 9

Leu Ala Gly Leu Ile Asp Ala Asp Gly
1               5

<210> SEQ ID NO 10
<211> LENGTH: 71
<212> TYPE: DNA
<213> ORGANISM: Arabidopsis thaliana

<400> SEQUENCE: 10
ctcttgaact tccaagagt tgaagaaaat cacagaaagc cttagcacag agaagagaga    60
ttgaagaagt c                                                       71

<210> SEQ ID NO 11
<211> LENGTH: 256
<212> TYPE: DNA
<213> ORGANISM: Arabidopsis thaliana

<400> SEQUENCE: 11
agaggatata tatgtacata tgcaaaggga tatcaagacc atctgtaatc ttttgaagtt    60
ttgtgaagct atagaagcca agcaagaatt ctaccagatt acttcccaaa taagtggtgt   120
gaatgtaaat taataagagc tacagaaaca ttgattggct cagtgtatgt gttgtattca   180
tattcgttgt tttattttat acggttgaga attgaataat gttgttgcat caaatcacta   240
tgaaggacat ttacag                                                  256

<210> SEQ ID NO 12
<211> LENGTH: 143
<212> TYPE: DNA
<213> ORGANISM: Arabidopsis thaliana

<400> SEQUENCE: 12
ctcaattttg gactcgtctg cttttgttta tataaacact tctcttcttc ttcaatctcc    60
acacacacca cacaaaacca cctaccttct tcgatttctc cagaaatcct ccttcaagtt   120
catactcatg gaagaagcta aag                                          143

<210> SEQ ID NO 13
<211> LENGTH: 295
<212> TYPE: DNA
<213> ORGANISM: Arabidopsis thaliana

<400> SEQUENCE: 13
agcacttctc cattaccaca ttcttcttct tcttctcctt catgatggta attagaagta    60
gtagaagaag aactgcactt gctttaactt aaataaatct ctgttcaaa ttgttcattt   120 taaaaacaga aggaaacgaa aaaaaaaatc aatttcggtt cttgttgaca cgatttgtaa   180
tttcttttct tcatttgaat tgaactggta aatactttct tctctgtcaa aatctttatt   240
ttctattttc tgtacaaggc caagttcttc actaataaat cgaattgttt ttcta       295

<210> SEQ ID NO 14
<211> LENGTH: 172
<212> TYPE: DNA
<213> ORGANISM: Arabidopsis thaliana

<400> SEQUENCE: 14
agaaaaaaat aaaagagtga gaaaaatcgt agagctatat attcgcacat gtactcgttt    60
cgctttcctt agtgttagct gctgccgctg ttgtttctcc tccatttctc tatctttctc   120
tctcgctgct tctcgaatct tctgtatcat cttcttcttc ttcaagtgaa aa            172

<210> SEQ ID NO 15
<211> LENGTH: 394
<212> TYPE: DNA
<213> ORGANISM: Arabidopsis thaliana

<400> SEQUENCE: 15
gtgtgtcttg tcttatctgg ttcgtggtgg tgagtttgtt acaaaaaaat ctattttccc    60
tagttgagat gggaattgaa ctatctgttg ttatgtggat tttattttct tttttctctt   120
tagaacctta tggttgtgtc aagaagtctt gtgtacttta gttttatatc tctgttttat   180
ctcttctatt ttctttagga tgcttgtgat gatgctgttt ttttttgtcc ctaagcaaaa   240
aaatatcata ttatatttgg tccttggttc attttttttgg tttttttttg tcttcacata   300
taaatattgt ttgaatgtct tcaatctttt atttgtatga gacaattatt taagtatcgg   360
gtgacaatgc agctattatg tattgtcgat tgtt                               394

<210> SEQ ID NO 16
<211> LENGTH: 45
<212> TYPE: DNA
<213> ORGANISM: Arabidopsis thaliana

<400> SEQUENCE: 16
tgtccccaaa gtctcctctt ccttatctct tggaaaccaa gaagc                    45

<210> SEQ ID NO 17
<211> LENGTH: 228
<212> TYPE: DNA
<213> ORGANISM: Arabidopsis thaliana

<400> SEQUENCE: 17
aattattagg acactacctg tctatctttg tgtatatgta tgtatggttg cataaagata    60
ctacgaactt ttatcgttag tattgtgtct ctgtttcagc ttttaatgta aaatagcttg   120
ggggtattat ctttgtagca ttgaatgctt aagatgataa tatgatatga ttatcaaatt   180
attataagtt ggaacttgga ataatagaaa ttttatatgt tttatatt                228

<210> SEQ ID NO 18
<211> LENGTH: 48
<212> TYPE: DNA
<213> ORGANISM: Artificial Sequence
<220> FEATURE:
<223> OTHER INFORMATION: mutated sequence

<400> SEQUENCE: 18
ttagcttgtt ccacattttt attttaagct atgtcatgct gggtcaga                 48

<210> SEQ ID NO 19
<211> LENGTH: 47
<212> TYPE: DNA
<213> ORGANISM: Artificial Sequence
<220> FEATURE:
<223> OTHER INFORMATION: mutated sequence

<400> SEQUENCE: 19
ttagcttgtt ccacattttt atttaagcta tgtcatgctg ggtcaga                  47

<210> SEQ ID NO 20
<211> LENGTH: 45
<212> TYPE: DNA

```
<213> ORGANISM: Artificial Sequence
<220> FEATURE:
<223> OTHER INFORMATION: mutated sequence

<400> SEQUENCE: 20
ttagcttgtt ccacattttt ataagctatg tcatgctggg tcaga                45

<210> SEQ ID NO 21
<211> LENGTH: 42
<212> TYPE: DNA
<213> ORGANISM: Artificial Sequence
<220> FEATURE:
<223> OTHER INFORMATION: mutated sequence

<400> SEQUENCE: 21
ttagcttgtt ccacattttt atttatgtca tgctgggtca ga                   42

<210> SEQ ID NO 22
<211> LENGTH: 38
<212> TYPE: DNA
<213> ORGANISM: Artificial Sequence
<220> FEATURE:
<223> OTHER INFORMATION: mutated sequence

<400> SEQUENCE: 22
ttagcttgtt ccacattttt atgtcatgct gggtcaga                        38

<210> SEQ ID NO 23
<211> LENGTH: 24
<212> TYPE: DNA
<213> ORGANISM: Artificial Sequence
<220> FEATURE:
<223> OTHER INFORMATION: mutated sequence

<400> SEQUENCE: 23
ttagctatgt catgctgggt caga                                       24
```